(12) United States Patent
Prante et al.

(10) Patent No.: US 11,180,511 B2
(45) Date of Patent: Nov. 23, 2021

(54) DIAGNOSIS, TREATMENT AND PREVENTION OF NEUROTENSIN RECEPTOR-RELATED CONDITIONS

(71) Applicants: Friedrich-Alexander-Universitat Erlangen-Nurnberg, Erlangen (DE); Universitatsklinikum Erlangen, Erlangen (DE)

(72) Inventors: Olaf Prante, Erlangen (DE); Torsten Kuwert, Mohrendorf (DE); Peter Gmeiner, Buckenhof (DE); Ashutosh Banerjee, Berlin (DE); Simone Maschauer, Erlangen (DE)

(73) Assignee: Friedrich-Alexander-Universität Erlangen-Nürnberg; Universitätsklinikum Erlangen, Erlangen (DE)

( * ) Notice: Subject to any disclaimer, the term of this patent is extended or adjusted under 35 U.S.C. 154(b) by 235 days.

(21) Appl. No.: 16/322,715

(22) PCT Filed: Aug. 2, 2017

(86) PCT No.: PCT/EP2017/069570
§ 371 (c)(1),
(2) Date: Feb. 1, 2019

(87) PCT Pub. No.: WO2018/024789
PCT Pub. Date: Feb. 8, 2018

(65) Prior Publication Data
US 2020/0377523 A1 Dec. 3, 2020

(30) Foreign Application Priority Data
Aug. 3, 2016 (EP) .................................... 16182597

(51) Int. Cl.
*C07K 5/00* (2006.01)
*A61K 51/04* (2006.01)
*C07F 5/00* (2006.01)

(52) U.S. Cl.
CPC .......... *C07F 5/003* (2013.01); *A61K 51/0478* (2013.01)

(58) Field of Classification Search
CPC ............................ C07F 5/003; A61K 51/0478
See application file for complete search history.

(56) References Cited

U.S. PATENT DOCUMENTS

| 4,885,363 | A | | 12/1989 | Tweedle et al. |
| 5,021,556 | A | | 6/1991 | Srinivasan |
| 5,075,099 | A | | 12/1991 | Srinivasan et al. |
| 5,364,613 | A | | 11/1994 | Sieving et al. |
| 5,367,080 | A | | 11/1994 | Toner et al. |
| 5,420,141 | A | | 5/1995 | Boigegrain et al. |
| 5,720,934 | A | | 2/1998 | Dean et al. |
| 5,886,142 | A | | 3/1999 | Thakur et al. |
| 5,925,661 | A | * | 7/1999 | Labeeuw ............. C07D 401/12 514/376 |
| 8,580,231 | B2 | * | 11/2013 | Sukerkar ................. C01F 17/20 424/9.363 |
| 2007/0213302 | A1 | | 9/2007 | McElroy et al. |

FOREIGN PATENT DOCUMENTS

| RU | 2066317 | 9/1996 |
| RU | 2195455 C2 | 12/2002 |
| WO | WO2007106721 A2 | 9/2007 |
| WO | WO 2009/109332 A1 | 9/2009 |
| WO | WO2011156557 A2 | 12/2011 |
| WO | WO 2014/086499 A1 | 6/2014 |

(Continued)

OTHER PUBLICATIONS

Nan Ma et al. The application of click chemistry in the synthesis of agents with anticancer activity, Drug Design Development and Therapy, 9, 1585-1599. (Year: 2015).*
PCT International Search Report and Written Opinion for International Application No. PCT/EP2017/069570, dated Oct. 13, 2017, 11 pages.
Myers et al., "Cancer, Chemistry, and the Cell: Molecules that Interact with the Neurotensin Receptors", ACS Chemical Biology, vol. 4, No. 7, May 22, 2009, pp. 503-525.
Valerie et al., "Inhibition of Neurotensin Receptor 1 Selectively Sensitizes Prostate Cancer to Ionizing Radiation", Cancer Research, vol. 71, No. 21, Nov. 1, 2011, pp. 6817-6826.

(Continued)

*Primary Examiner* — Michael G. Hartley
*Assistant Examiner* — Jagadishwar R Samala
(74) *Attorney, Agent, or Firm* — Patterson Thuente Pedersen, P.A.

(57) ABSTRACT

The present invention describes a compound of formula (I) which can be used in the diagnosis, treatment or prevention of neurotensin receptor-related conditions such as tumors and hematological malignancies.

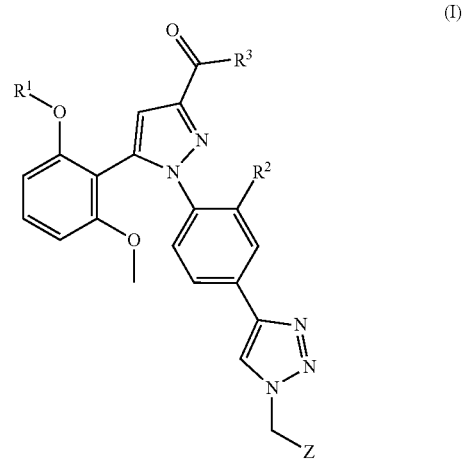

(I)

19 Claims, 2 Drawing Sheets

(56) References Cited

FOREIGN PATENT DOCUMENTS

| WO | WO2014086499 | * | 6/2014 | |
| WO | WO-2014086499 A1 | * | 6/2014 | ........... C07D 231/14 |

OTHER PUBLICATIONS

McNaught et al., "Chelation" In: "Copendium of Chemical Terminology, IUPAC Recommendations, Second Edition", Blackwell Science, Oxford, Jan. 1, 1997, p. 68.

Extended European Search Report for European Application No. 16182597.1, dated Oct. 14, 2016, 8 pages.

Kinkead et al., "Neurotensin, Schizophrenia, and Antipsychotic Drug Action", International Review of Neurobiology (2004), vol. 59, pp. 327-349 (the year of publication is sufficiently earlier than the effective U.S. filing date and any foreign priority date so that the particular month of publication is not in issue).

Ferraro et al., "Emerging Evidence for Neurotensin Receptor 1 Antagonists as Novel Pharmaceutics in Neurodegenerative Disorders", Mini-Reviews in Medicinal Chemistry, vol. 9, No. 12, Aug. 29, 2009, pp. 1429-1438.

Dupouy et al., "The potential use of the neurotensin high affinity receptor 1 as a biomarker for cancer progression and as a component of personalized medicine in selective cancers", Biochimie, vol. 93, No. 9, May 17, 2011, pp. 1369-1378.

Taylor et al., "Prostate Cancer Targeting Motifs: Expression of $\alpha_v\beta_3$, Neurotensin Receptor 1, Prostate Specific Membrane Antigen, and Prostate Stem Cell Antigen in Human Prostate Cancer Cell Lines and Xenografts", The Prostate, vol. 72, No. 5, Jul. 11, 2011, pp. 523-532.

Swift et al., "Altered Expression of Neurotensin Receptors is Associated with the Differentiation State of Prostate Cancer", Cancer Research (2010), vol. 70, No. 1, pp. 347-356 (the year of publication is sufficiently earlier than the effective U.S. filing date and any foreign priority date so that the particular month of publication is not in issue).

Maschauer et al., "Synthesis of a $^{68}$Ga-Labeled Peptoid—Peptide Hybrid for Imaging of Neurotensin Receptor Expression in Vivo", ACS Medicinal Chemistry Letters, vol. 1, No. 5, May 21, 2010, pp. 224-228.

Maina et al., "[$^{99m}$Tc]Demotensin 5 and 6 in the NTS1-R-targeted imaging of tumours: synthesis and preclinical results", Journal of Nuclear Medicine and Molecular Imaging, vol. 34, No. 11, Jun. 27, 2007, pp. 1804-1814.

Maschauer et al., "$^{18}$F- and $^{68}$Ga-Labeled Neurotensin Peptides for PET Imaging of Neurotensin Receptor 1", Journal of Medicinal Chemistry, vol. 59, Jun. 23, 2016, pp. 6480-6492.

Lang et al., "Synthesis and Evaluation of a $^{18}$F-Labeled Diarylpyrazole Glycoconjugate for the Imaging of NTS1-Positive Tumors", Journal of Medicinal Chemistry, vol. 56, No. 22, Oct. 25, 2013, pp. 9361-9365.

Schulz et al., "Comparative Evaluation of the Biodistribution Profiles of a Series of Nonpeptidic Neurotensin Receptor-1 Antagonists Reveals a Promising Candidate for Theranostic Applications", The Journal of Nuclear Medicine, vol. 57, No. 7, Mar. 3, 2016, pp. 1120-1123.

O'Toole et al., "The analysis of quantitative expression of somatostatin and dopamine receptors in gastro-entero-pancreatic tumours opens new therapeutic strategies", European Journal of Endocrinology (2006), vol. 155, pp. 849-857 (the year of publication is sufficiently earlier than the effective U.S. filing date and any foreign priority date so that the particular month of publication is not in issue).

Berge et al., "Pharmaceutical Salts", Journal of Pharmaceutical Sciences, vol. 66, No. 1, Jan. 1977, 19 pages.

Dumelin et al., "A Portable Albumin Binder from a DNA-Encoded Chemical Library", Angewandte Chemie International Edition, vol. 47, No. 17, Mar. 13, 2008, pp. 3196-3201.

Banerjee et al., "New directions in the coordination chemistry of $^{99m}$Tc: a reflection on technetium core structures and a strategy for new chelate design", Nuclear Medicine and Biology (2005), vol. 32, pp. 1-20 (the year of publication is sufficiently earlier than the effective U.S. filing date and any foreign priority date so that the particular month of publication is not in issue).

Wadas et al., "Coordinating Radiometals of Copper, Gallium, Indium, Yttrium, and Zirconium for PET and SPECT Imaging of Disease", Chemical Reviews, vol. 110, No. 5, Apr. 23, 2010, pp. 2858-2902.

Doulias et al., "Endosomal and Lysosomal Effects of Desferrioxamine: Protection of HeLa Cells from Hydrogen Peroxide-Induced DNA Damage and Induction of Cell-Cycle Arrest", Free Radical Biology & Medicine (2003), vol. 35, No. 7, pp. 719-728 (the year of publication is sufficiently earlier than the effective U.S. filing date and any foreign priority date so that the particular month of publication is not in issue).

Schwartz et al., "Preparation of Hydrazino-Modified Proteins and Their Use for the Synthesis of $^{99m}$Tc-Protein Conjugates", Bioconjugate Chemistry (1991), vol. 2, No. 5, pp. 333-336 (the year of publication is sufficiently earlier than the effective U.S. filing date and any foreign priority date so that the particular month of publication is not in issue).

Babich et al., "Technetium-99m-Labeled Hydrazino Nicotinamide Derivatized Chemotactic Peptide Analogs for Imaging Focal Sites of Bacterial Infection", The Journal of Nuclear Medicine, vol. 34, No. 11, Nov. 1993, pp. 1964-1974.

Babich et al., "Effect of "Co-ligand" on the Biodistribution of $^{99m}$Tc-labeled Hydrazino Nicotinic Acid Derivatized Chemotactic Peptides", Nuclear Medicine and Biology, vol. 22, No. 1, Jan. 1995, pp. 25-30.

Brechbiel et al., "Backbone-Substituted DTPA Ligands for $^{90}$Y Radioimmunotherapy", Bioconjugate Chemistry (1991), vol. 2, No. 3, pp. 187-194 (the year of publication is sufficiently earlier than the effective U.S. filing date and any foreign priority date so that the particular month of publication is not in issue).

Li et al., "Development of an in vitro model for assessing the in vivo stability of lanthanide chelates", Nuclear Medicine and Biology (2001), vol. 28, pp. 145-154 (the year of publication is sufficiently earlier than the effective U.S. filing date and any foreign priority date so that the particular month of publication is not in issue).

Eisenwiener et al., "NODAGATOC, a New Chelator-Coupled Somatostatin Analogue Labeled with [$^{67/68}$Ga] and [$^{111}$In] for SPECT, PET, and Targeted Therapeutic Applications of Somatostatin Receptor (hsst2) Expressing Tumors", Bioconjugate Chemistry, vol. 13, No. 3, Apr. 23, 2002, pp. 530-541.

Nock et al., "CCK-2/Gastrin Receptor-Targeted Tumor Imaging with $^{99m}$Tc-Labeled Minigastrin Analogs", The Journal of Nuclear Medicine, vol. 46, No. 10, Oct. 2005, pp. 1727-1736.

Brasse et al., "Radiometals: towards a new success story in nuclear imaging?", The Royal Society of Chemistry, Dalton Transactions (2015), vol. 44, pp. 4845-4858 (the year of publication is sufficiently earlier than the effective U.S. filing date and any foreign priority date so that the particular month of publication is not in issue).

Cai et al., "Chelators for copper radionuclides in positron emission tomography radiopharmaceuticals", Journal of Labelled Compounds and Radiopharmaceuticals, vol. 57, Dec. 18, 2013, pp. 224-230.

Deri et al., "PET imaging with $^{89}$Zr: From radiochemistry to the clinic", Nuclear Medicine and Biology (2013), vol. 40, No. 1, pp. 3-14 (the year of publication is sufficiently earlier than the effective U.S. filing date and any foreign priority date so that the particular month of publication is not in issue).

Price et al., "Matching chelators to radiometals for radiopharmaceuticals", The Royal Society of Chemistry, Chemistry Society Reviews, vol. 43, Oct. 30, 2013, pp. 260-290.

Lang et al., "Efficient Synthesis of Heterocyclic Neurotensin Receptor Ligands by Microwave-Assisted Aminocarbonylation", Synthesis, vol. 45, Nov. 7, 2013, pp. 2474-2480.

Suchy et al., ""Click" chemistry toward bis(DOTA-derived) heterometallic complexes: potential bimodal MRI/PET(SPECT) molecular imaging probes", The Royal Society of Chemistry, RSC Advances, vol. 3, No. 10, Jan. 9, 2013, pp. 3249-3259.

(56) References Cited

OTHER PUBLICATIONS

Struthers et al., "Metal chelating systems synthesized using the copper(I) catalyzed azide-alkyne cycloaddition", The Royal Society of Chemistry, Dalton Transactions, vol. 39, No. 3, Nov. 23, 2009, pp. 675-996.
Chinchilla et al., "The Sonogashira Reaction: A Booming Methodology in Synthetic Organic Chemistry", Chemical Reviews, vol. 107, No. 3, Feb. 17, 2007, pp. 874-922.
Sparr et al, "Syntheses, Receptor Bindings, in vitro and in vivo Stabilities and Biodistributions of DOTA-Neurotensin (8-13) Derivatives Containing β-Amino Acid Residues—A Lesson about the Importance of Animal Experiments", Chemistry & Biodiversity (2013), vol. 10, pp. 2101-2121 (the year of publication is sufficiently earlier than the effective U.S. filing date and any foreign priority date so that the particular month of publication is not in issue).
Russian Office Action dated Sep. 10, 2020 in Application No. 2019104888, 10 pages.
Federal Service on Intellectual Property Federal State Budgetary Enterprise "Federal Institute of Industrial Property" (FIPS), Search Report dated Sep. 10, 2020 in Application No. 2019104888, 2 pages.

\* cited by examiner

DIAGNOSIS, TREATMENT AND PREVENTION OF NEUROTENSIN RECEPTOR-RELATED CONDITIONS

RELATED APPLICATIONS

This application is a national stage filing under 35 U.S.C. § 371 of International Application No. PCT/EP2017/069570, filed Aug. 2, 2017, which claims priority under 35 U.S.C. § 119 to European Patent Application No. 16182597.1, filed Aug. 3, 2016, the disclosures of which are each incorporated herein by reference in their entirety.

FIELD OF THE INVENTION

The present invention relates to radionuclide containing chemical compounds that exhibit activity at neurotensin receptors which can be used in the diagnosis, treatment and prevention of a variety of conditions, and to precursors thereof which do not contain the radionuclide. Furthermore, the present invention relates to a method of preparation of chemical compounds having such activities and to the medical use of these compounds in the diagnosis, treatment and prevention of a variety of conditions.

BACKGROUND OF THE INVENTION

Cancer represents one of the main causes of death worldwide. Mortality is particularly high among patients suffering from prostate, colorectal, pancreas, lung, bronchial and breast carcinoma. Although some progress has been made in the last few years, the development of more potent compounds for the diagnosis, treatment and prevention of cancer remains a high priority and is required to tackle the growing number of deaths resulting from cancer.

Neurotensin receptors are transmembrane receptors that bind the neurotransmitter neurotensin. Among the three neurotensin receptor subtypes (NTS1-3), the G-protein coupled receptor NTS1 possesses the most suitable prerequisites to serve as a drug target (non-patent document 1). The NTS1 receptor is involved in a number of pathophysiological processes including neurodegenerative diseases such as schizophrenia (non-patent document 2) and Parkinson's disease (non-patent document 3). NTS1 overexpression has been demonstrated in various tumor types such as prostate, pancreas, colon and small cell lung carcinoma. The selective overexpression of NTS1 in tumors besides its apparently low expression in the corresponding healthy tissues thereby offers an outstanding opportunity to treat tumors by a targeted therapy approach. This is supported by various publications discussing NTS1 as a biomarker for the prognosis of different cancer types (non-patent document 4) and providing evidence for the overexpression of NTS1 in a number of cell types both in vitro and in vivo (non-patent documents 5 and 6).

The possibility to selectively address NTS1 overexpressing tumors in vivo has been also supported by several publications using radiolabeled agents for imaging of NTS1 receptors via positron emission tomography (PET) (exemplified by: non-patent documents 7 to 9). The treatment of small cell lung cancer with a small molecule NTS1 antagonist (Meclinertant, SR48692) failed due to a lack of efficacy, demonstrating that the therapy of tumors by blocking NTS1 receptors with an antagonist as the mechanism of action did not turn out to be successful. Nevertheless, SR48692 is able to sensitize tumors for radiotherapy (non-patent document 10).

A non-peptide $^{18}$F-labeled NTS1 tracer for PET imaging of NTS1 positive tumors has been described by the present inventors (non-patent document 11) and a non-peptide SPECT tracer labeled with In-111 has been described by Schulz et al. (non-patent document 12), The presence of dopamine receptors in pancreatic tumors has been described (non-patent document 13). Therefore, radiotracers that bind to both dopamine receptors and NTS1 cannot be used for studying or staging NTS1-positive tumors adequately, because of the interfering signal from dopamine receptor binding.

Non-Patent Documents

Non-patent document 1: Cancer Chemistry and Cell: Molecules that interact with Neurotensin Receptors; Myers, Rebecca M.; Shearman, James W.; Kitching, Matthew O.; Ramos-Montoya, Antonio; Neal, David E.; Ley, Steven V.; ACS Chemical Biology (2009), 4(7), 503-525.

Non-patent document 2: Neurotensin, schizophrenia, and antipsychotic drug action; Kinkead, Becky; Nemeroff, Charles B.; International Review of Neurobiology (2004), 59, 327-349.

Non-patent document 3: Emerging evidence for neurotensin receptor 1 antagonists as novel pharmaceutics in neurodegenerative disorders; Ferraro, L.; Tomasini, M. C.; Beggiato, S.; Guerrini, R.; Salvadori, S.; Fuxe, K.; Calza, L.; Tanganelli, S.; Antonelli, T.; Mini-Reviews in Medicinal Chemistry (2009), 9(12), 1429-1438.

Non-patent document 4: The potential use of the neurotensin high affinity receptor 1 as a biomarker for cancer progression and as a component of personalized medicine in selective cancers; Dupouy, Sandra; Mourra, Najat; Doan, Van Kien; Gompel, Anne; Alifano, Marco; Forgez, Patricia.; Biochimie (2011), 93(9), 1369-1378.

Non-patent document 5: Prostate cancer targeting motifs: Expression of $\alpha_v\beta_3$, neurotensin receptor 1, prostate specific membrane antigen, and prostate stem cell antigen in human prostate cancer cell lines and xenografts; Taylor, Robert M.; Severns, Va.; Brown, David C.; Bisoffi, Marco; Sillerud, Laurel O.; Prostate (2012), 72(5), 523-532.

Non-patent document 6: Altered Expression of Neurotensin Receptors Is Associated with the Differentiation State of Prostate Cancer; Swift, Stephanie L., Burns, Julie E., Maitland, Norman J.; Cancer Research (2010), 70(1), 347-356.

Non-patent document 7: Synthesis of a $^{68}$Ga-Labeled Peptoid-Peptide Hybrid for Imaging of Neurotensin Receptor Expression in Vivo; Maschauer, Simone; Einsiedel, Jurgen; Hocke, Carsten; Hubner, Harald; Kuwert, Torsten; Gmeiner, Peter; Prante, Olaf; ACS Medicinal Chemistry Letters (2010), 1(5), 224-228.

Non-patent document 8: [$^{99m}$Tc] Demotensin 5 and 6 in the NTS1-R-targeted imaging of tumors: synthesis and preclinical results; Maina, Theodosia; Nikolopoulou, Anastasia; Stathopoulou, Eleni; Galanis, Athanassios S.; Cordopatis, Paul; Nock, Berthold A; European Journal of Nuclear Medicine and Molecular Imaging (2007), 34(11), 1804-1814.

Non-patent document 9: $^{18}$F- and $^{68}$Ga-labeled Neurotensin Peptides for PET Imaging of Neurotensin Receptor 1; Maschauer S., Einsiedel J., Hubner H., Gmeiner P., Prante O.; Journal of Medicinal Chemistry (2016).

Non-patent document 10: Inhibition of Neurotensin Receptor 1 Selectively Sensitizes Prostate Cancer to Ionizing Radiation; Valerie, Nicholas C. K.; Casarez, Eli V.; DaSilva, John O.; Dunlap-Brown, Marya E.; Parsons, Sarah J.; Amorino, George P.; Dziegielewski, Jaroslaw; Cancer Research (2011), 71(21), 6817-6826.

Non-patent document 11: Synthesis and Evaluation of a $^{18}$F-Labeled Diarylpyrazole Glycoconjugate for the Imaging of NTS1-Positive Tumors; Lang, Christopher; Maschauer, Simone; Hubner, Harald; Gmeiner, Peter; Prante, Olaf; Journal of Medicinal Chemistry (2013), 56(22), 9361-9365.

Non-patent document 12: Comparative Evaluation of the Biodistribution Profiles of a Series of Nonpeptidic Neurotensin Receptor-1 Antagonists Reveals a Promising Candidate for Theranostic Applications; Schulz, J., Rohracker, M., Stiebler, M., Goldschmidt, J., Grosser, O., Osterkamp, F., Pethe, A., Reineke, U., Smerling, C., and Amthauer, H.; Journal of Nuclear Medicine (2016), 57, 1120-1123.

Non-patent document 13: The analysis of quantitative expression of somatostatin and dopamine receptors in gastro-entero-pancreatic tumours opens new therapeutic strategies; O'Toole, D., Saveanu, A., Couvelard, A., Gunz, G., Enjalbert, A., Jaquet, P., Ruszniewski, P., Barlier, A.; European Journal of Endocrinology (2006), 155, 849-857.

SUMMARY OF THE INVENTION

The present invention relates to compounds of formula (I) comprising a non-peptide NTS1 antagonist and a chelator that is linked to the antagonist.

In view of the problems in the prior art, it was an object of the present invention to develop radiopharmaceuticals that show low binding to dopamine receptors and improved selectivity for NTS1. The present inventors developed new compounds which overcome these problems and show an improved selectivity for NTS1 receptors over dopamine receptors. This increased selectivity not only results in more potent activities but also enables the diagnosis and imaging of NTS1-positive tumors, e.g., by reducing the interference caused by dopamine receptor binding.

The present inventors have surprisingly found that the triazolyl moiety reduces the affinity of these compounds to dopamine receptors and leads to an increased tumor growth inhibition in vivo when compared to corresponding amide analogues.

Furthermore, the compounds of the present invention show subnanomolar affinity to NTS1, low affinity to dopamine receptors, selective concentration of the ligand in NTS1 overexpressing tumors, fast washout from healthy tissue and high uptake into tumors thus leading to a high dose of deposited radioactivity in the tumor with concomitant acceptable doses in healthy tissues.

DEFINITIONS

Figure 1:
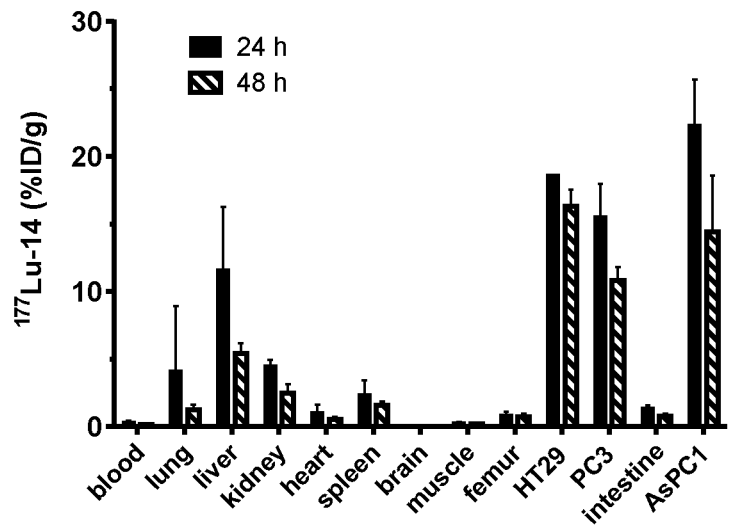
FIG. 1 shows the accumulation of radioactivity in NTS1 receptor-positive tumors (HT29, PC3, AsPC1) which was high at 24 and 48 h p.i. with excellent tumor retention over time, whereas the uptake in non-targeted tissue (e.g., blood, liver and bones) was significantly lower and showed a fast clearance rate.

As used herein, the term "alkyl" refers to a monovalent saturated acyclic (i.e., non-cyclic) hydrocarbon group which may be linear or branched. Accordingly, an "alkyl" group does not comprise any carbon-to-carbon double bond or any carbon-to-carbon triple bond. A "$C_{1-6}$ alkyl" denotes an alkyl group having 1 to 6 carbon atoms. Preferred exemplary alkyl groups are methyl, ethyl, propyl (e.g., n-propyl or isopropyl), or butyl (e.g., n-butyl, isobutyl, sec-butyl, or tert-butyl).

As used herein, the term "alkylene" refers to an alkanediyl group, i.e. a divalent saturated acyclic hydrocarbon group which may be linear or branched. A "$C_{1-3}$ alkylene" denotes an alkylene group having 1 to 3 carbon atoms. Preferred exemplary alkylene groups are methylene (—$CH_2$—), ethylene (e.g., —$CH_2$—$CH_2$— or —CH(—$CH_3$)—) or propylene (e.g., —$CH_2$—$CH_2$—$CH_2$—, —CH(—$CH_2$—$CH_3$)—, —$CH_2$—CH(—$CH_3$)—, or —CH(—$CH_3$)—$CH_2$—).

As used herein, the term "cycloalkyl" refers to a saturated hydrocarbon ring group, including monocyclic rings as well as bridged ring, spiro ring and/or fused ring systems (which may be composed, e.g., of two or three rings; such as, e.g., a fused ring system composed of two or three fused rings). "Cycloalkyl" may, e.g., refer to cyclopropyl, cyclobutyl, cyclopentyl, cyclohexyl, cycloheptyl, or adamantyl.

"Halogen" represents F, Cl, Br and I, more preferably F or C, even more preferably F.

The term "heteroarylene" refers to a divalent five or six-membered aromatic ring, wherein one or more of the carbon atoms in the ring have been replaced by 1, 2 or 3 of the same or different heteroatoms selected from N, O and S. Examples of the heteroarylene group include furan, thiophene, pyridine, pyrimidine, pyridazine, pyrazine, pyrrole, imidazole, pyrazole, thiazole, isothiazole, oxazole, isoxazole, oxadiazole, thiadiazole, triazole, tetrazole, triazine and the like.

As used herein, the terms "optional", "optionally" and "may" denote that the indicated feature may be present but can also be absent. Whenever the term "optional", "optionally" or "may" is used, the present invention specifically relates to both possibilities, i.e., that the corresponding feature is present or, alternatively, that the corresponding feature is absent. For example, the expression "X is optionally substituted with Y" (or "X may be substituted with Y") means that X is either substituted with Y or is unsubstituted. Likewise, if a component of a composition is indicated to be "optional", the invention specifically relates to both possibilities, i.e., that the corresponding component is present (contained in the composition) or that the corresponding component is absent from the composition.

If a compound or moiety is referred to as being "optionally substituted" it can in each instance include one or more of the indicated substituents, whereby the substituents can be the same or different.

The term "pharmaceutically acceptable salt" refers to a salt of a compound of the present invention. Suitable pharmaceutically acceptable salts include acid addition salts which may, for example, be formed by mixing a solution of compounds of the present invention with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/ diphosphate, picrate, pivalate, polygalacturonate, propionate, salicylate, stearate, sulfate, subacetate, succinate, tannate, tartrate, teoclate, tosylate, triethiodide, undecanoate, valerate, and the like (see, for example, S. M. Berge et al., "Pharmaceutical Salts", J. Pharm. Sci., 66, pp. 1-19 (1977)).

DETAILED DESCRIPTION OF THE INVENTION

The present invention relates to a compound of formula (I), optionally in the form of a pharmaceutically acceptable salt, solvate, ester, polymorph, tautomer, racemate, enantiomer, diastereomer or mixture thereof

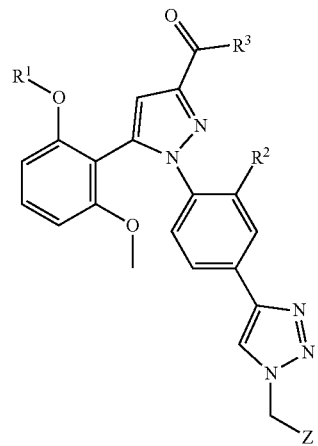
(I)

In the compound of formula (I), $R^1$ is selected from the group consisting of -hydrogen, —($C_{1-6}$ alkyl), —($C_{3-6}$ cycloalkyl) and —($C_{1-3}$ alkylene-$C_{3-6}$ cycloalkyl), wherein $C_{1-6}$ alkyl, $C_{3-6}$ cycloalkyl and the $C_{1-3}$ alkylene and $C_{3-6}$ cycloalkyl in ($C_{1-3}$ alkylene-$C_{3-6}$ cycloalkyl) may be substituted with one or more halogen atoms. $R^1$ is preferably —($C_{1-3}$ alkyl) or —$CH_2$-cyclopropyl. $R^1$ is more preferably —($C_{1-3}$ alkyl).

$R^2$ is selected from -hydrogen, -halogen, nitro, —($C_{1-6}$ alkyl), —($C_{3-6}$ cycloalkyl) and —($C_{1-3}$ alkylene-$C_{3-6}$ cycloalkyl), wherein $C_{1-6}$ alkyl, $C_{3-6}$ cycloalkyl and the $C_{1-3}$ alkylene and $C_{3-6}$ cycloalkyl in ($C_{1-3}$ alkylene-$C_{3-6}$ cycloalkyl) may be substituted with one or more halogen atoms. $R^2$ is preferably -halogen, nitro or —($C_{1-6}$ alkyl), wherein the $C_{1-6}$ alkyl is optionally substituted with one or more fluorine. $R^2$ is more preferably —($C_{1-6}$ alkyl).

$R^3$ is selected from 2-amino-2-adamantane carboxylic acid, cyclohexylglycine and 9-amino-bicyclo[3.3.1]nonane-9-carboxylic acid. $R^3$ is preferably a group having the following formula

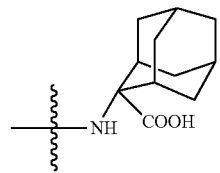

The Group Z

Z may be any group which comprises a chelator. It is preferred that Z in formula (I) does not comprise a radionuclide as defined in the present invention, unless otherwise specified.

Z preferably comprises a linker group and a chelator group. More preferably, Z is -(linker group)-(chelator group). The linker group and the chelator group are preferably as defined below.

The group Z may also comprise one or two or three groups of the following partial structure:

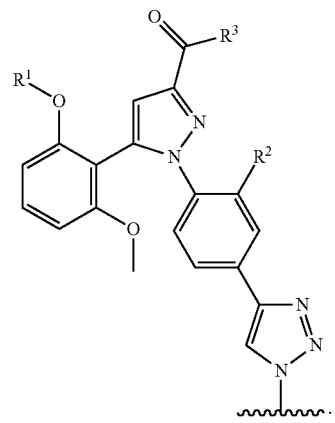

In these partial structures, the definitions of $R^1$, $R^2$ and $R^3$ are independently as defined above with respect to formula (I). If group Z comprises such partial structures, the compound of formula (I) forms a multimeric structure which is expected to show enhanced avidity to the neurotensin receptor, probably due to the accumulated strength of multiple affinities of more than one non-covalent binding interaction with the receptor. The most important beneficial effects of such a multimeric structure could be improved tumor uptake in vivo, and also significantly improved tumor retention, and thereby improved imaging and therapy properties in comparison with monomers.

The Linker Group

Linker groups, which are commonly also referred to as spacers, are groups which separate two parts of a molecule. In the present invention, the linker group forms covalent bonds with both the chelator group and the part of the structure of formula (I) which is different from Z. The linker group may, in principle, be any chemical group which is capable of forming bonds with both the chelator group and the part of the structure of formula (I) which is different from Z. It is preferred that the linker group does not itself bind to a neurotensin receptor. Preferably, the linker group contains only atoms selected from H, B, C, N, O, F, Si, P, S, Cl, Br and I, which are preferably different from the radionuclides defined herein.

Examples of linker groups which can be used in the present invention contain one or more groups selected from —N($R^4$)—, —$C_{1-10}$ alkylene-, —C(O)—, —O—, -heteroarylene-, -phenylene-, —S—, —S(O)— and —S(O)$_2$—, wherein each $R^4$ is independently selected from hydrogen and $C_{1-6}$ alkyl, each $C_{1-10}$ alkylene is independently optionally substituted with one or more selected from halogen, C(O)OH and OH, each heteroarylene is independently 4 to 6 membered heteroarylene comprising 1 to 3 heteroatoms selected from N, O and S and the heteroarylene is optionally substituted with one or more selected from halogen and $C_{1-6}$ alkyl, and each phenylene is optionally substituted with one or more selected from halogen and $C_{1-6}$ alkyl.

Furthermore, the linker group may comprise one or two or three side chains which can be attached to the main chain of the linker group by replacing one or two or three hydrogen residues, preferably in a —$C_{1-10}$ alkylene-moiety, in the main chain of the linker group by the side chain(s). These side chains may comprise 1 to 10, preferably 1 to 8, groups selected from —N($R^4$)—, —$C_{1-10}$ alkylene-, —C(O)—, —O—, -heteroarylene-, -phenylene-, —S—, —S(O)— and —S(O)$_2$— and are terminated by —H, wherein the definitions of $R^4$ and the optional substituents of the other groups are as defined for the main chain of the linker group.

The linker group preferably consists of one or more groups selected from —N($R^4$)—, —$C_{1-10}$ alkylene-, —C(O)—, —O—, -heteroarylene-, -phenylene-, —S—, —S(O)— and —S(O)$_2$—.

In the present invention, it is preferred that the linker group comprises or consists of 3 to 15, more preferably 3 to 12, even more preferably 3 to 10 and most preferably 4 to 8 of the above groups.

Furthermore, as will be apparent to a skilled person, two adjacent groups in the linker group should be chosen so as to avoid a direct bond between two groups which would result in a partial structure which is not stable, in particular, in an aqueous medium at 25° C. and a pressure of 1 atm. From this standpoint, combinations such as —N($R^4$)—N($R^4$)—, —C(O)—C(O)—, —O—O—, —S—S—, —S(O)—S(O)—, —S(O)$_2$—S(O)$_2$—, —N($R^4$)—O—, —O—N($R^4$)—, —N($R^4$)—S—, —S—N($R^4$)—, —N($R^4$)—S(O)—, —S(O)—N($R^4$)—, —C(O)—S—, —S—C(O)—, —C(O)—S(O)—, —S(O)—C(O)—, —C(O)—S(O)$_2$—, —S(O)$_2$—C(O)—, —S—O—, —O—S—, —S(O)—O—, —O—S(O)—, —S(O)—S—, —S—S(O)—, —S(O)$_2$—S—, —S—S(O)$_2$—, S(O)$_2$—S(O)— and —S(O)—S(O)$_2$— are preferably excluded.

Furthermore, it is preferred that the combinations —$C_{1-10}$ alkylene-$C_{1-10}$ alkylene-, -heteroarylene-heteroarylene- and -phenylene-phenylene- are excluded.

An example of a side chain of the linker group, which is of particular interest in the present invention, is the following:

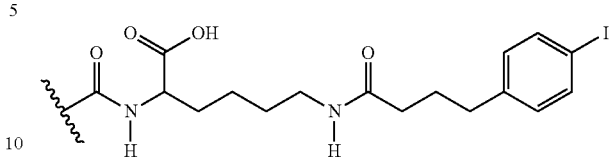

This group has been found to bind well to albumin and can be used to increase plasma half life and bioavailability of certain compounds (Angew. Chem., Int. Ed. 2008, 47(17) 3196-3201).

A more preferred class of linker groups is represented by —(X)$_p$—, wherein p is an integer from 1 to 10. Preferably, p is an integer from 1 to 8, 1 to 6, 1 to 5, 1 to 4 or 1 to 3.

Each X is preferably independently selected from
(a) —(N($R^4$)—$C_{1-10}$ alkylene)-,
(b) —(N($R^4$)-heteroarylene)-,
(c) —(N($R^4$)—C(O))—,
(d) —(O—$C_{1-10}$ alkylene)-,
(e) —(O-heteroarylene)-,
(f) —(O—C(O))—,
(g) —($C_{1-10}$ alkylene-heteroarylene)-,
(h) —($C_{1-10}$ alkylene-C(O))—,
(i) —(C(O)—$C_{1-10}$ alkylene)-,
(j) —(C(O)-heteroarylene)-,
(k) —(heteroarylene-$C_{1-10}$ alkylene)-,
(l) —(heteroarylene-C(O))—, and
(m) —($C_{1-10}$ alkylene)-.

In each X, $C_{1-10}$ alkylene is independently optionally substituted with one or more selected from halogen, C(O)OH and OH.

In each X, heteroarylene is 4 to 6-membered heteroarylene comprising 1 to 3 heteroatoms selected from N, O and S and the heteroarylene is optionally substituted with one or more selected from halogen and $C_{1-6}$ alkyl.

Each $R^4$ is independently selected from hydrogen and $C_{1-6}$ alkyl.

Especially preferred linker groups are selected from
(i) —$C_{1-10}$ alkylene-N($R^4$)—$C_{1-10}$ alkylene-N($R^4$)—C(O)—$C_{1-10}$ alkylene-N($R^4$)—,
(ii) —$C_{1-10}$ alkylene-N($R^4$)—$C_{1-10}$ alkylene-heteroarylene-$C_{1-10}$ alkylene-C(O)—$C_{1-10}$ alkylene-N($R^4$)—, and
(iii) —$C_{1-10}$ alkylene-N($R^4$)—$C_{1-10}$ alkylene-N($R^4$)—.

In these preferred examples, each $C_{1-10}$ alkylene is independently optionally substituted with one or more selected from halogen, C(O)OH and OH. The heteroarylene is 4 to 6-membered heteroarylene comprising 1 to 3 heteroatoms selected from N, O and S and the heteroarylene is optionally substituted with one or more selected from halogen and $C_{1-6}$ alkyl. Each $R^4$ is independently selected from hydrogen and $C_{1-6}$ alkyl. Preferably, each $R^4$ is independently selected from H, methyl, ethyl, n-propyl and iso-propyl.

The Chelator Group

The chelator group is a group capable of binding with and/or complexing a metal ion to form a heterocyclic ring including the metal ion. The metal ion includes metal ions which are defined as the radionuclides. Preferably, the chelator group contains only atoms selected from H, B, C, N, O, F, Si, P, S, C, Br and I, which are preferably different from the radionuclides defined herein.

Such chelators are known to the person skilled in the art. A wide variety of respective chelators is available and has been summarized by Banerjee et al. (Banerjee et al., Nucl. Med. Biol., 2005, 32, 1-20, and references therein, Wadas et al., Chem. Rev., 2010, 110, 2858-2902 and references therein). Such chelators include, but are not limited to linear, macrocyclic, tetrapyridine, $N_3S$, $N_2S2$ and $N_4$ chelators as disclosed in U.S. Pat. Nos. 5,367,080 A, 5,364,613 A, 5,021,556 A, 5,075,099 A and 5,886,142 A.

Further examples of suitable chelators are disclosed in U.S. Pat. No. 5,720,934 and by Doulias et al. (Doulias et al., Free Radio. Biol. Med., 2003, 35, 719-728).

The diagnostic and/or therapeutic use of some of the above chelators is described in the prior art. For example, 2-hydrazino nicotinamide (HYNIC) has been widely used in the presence of a coligand for incorporation of $^{99m}$Tc and $^{186,188}$Re (Schwartz et al., Bioconj. Chem., 1991, 2, 333-336; Babich et al., J. Nucl. Med., 1993, 34, 1964-1970; Babich et al., Nucl. Med. Biol., 1995, 22, 25-30). DTPA is used in Octreoscan® (Covidien), for complexing $^{111}$In and several modifications are described in the literature (Brechbiel et al., Bioconj. Chem., 1991, 2, 187-194; Li et al., Nucl Med. Biol, 2001, 28, 145-154). DOTA type chelators have been reported for radiotherapy applications by Tweedle et al. (U.S. Pat. No. 4,885,363). Certain polyaza macrocycles for chelating trivalent isotopes metals have been disclosed by Maecke et al. (Maecke et al., Bioconj. Chem., 2002, 13, 530-541). $N_4$-chelators such as a $^{99m}$Tc-$N_4$-chelator have been used for peptide labeling in the case of minigastrin for targeting CCK-2 receptors (Nock et al., J. Nucl Med., 2005, 46, 1727-1736).

Metal chelators for trivalent metals or pentavalent metals and their closely related analogs are, e.g., disclosed in WO 2009/109332 A1. The use of the above chelators for divalent and tetravalent radionuclides has been reported (Dalton Transactions 44, 11 (2015), 4845-4858; Journal of Labelled Compounds and Radiopharmaceuticals 57, 4 (2014), 224-230; Nuclear Medicine and Biology 40, 1 (2013), 3-14; and Chemical Society Reviews 43, 1 (2014), 260-290).

N'-{5-[Acetyl(hydroxy)amino]pentyl}-N-[5-({4-[(5-aminopentyl)(hydroxy)amino]-4-oxobutanoyl}amino)pentyl]-N-hydroxy-succinamide (DFO) has been reported as a particularly preferable chelator for Zr radionuclides (Nuclear Medicine and Biology 40, 1 (2013), 3-14).

The chelator group is preferably -(hydrocarbon group which contains from 8 to 40 carbon atoms, 2 to 12 nitrogen atoms and optionally 1 to 10 oxygen atoms and/or optionally 1 to 5 sulfur atoms and/or optionally 1 to 5 phosphor atoms).

Preferred examples of the chelator group comprise at least two groups selected from carboxylic acid, phosphinic acid, phosphonic acid and hydroxylamine.

Preferred examples of the chelator group are selected from 1,4,7,10-tetraazacyclododecane-1,4,7,10-tetraacetic acid (DOTA), 2,2',2"-(1,4,7-triazonane-1,4,7-triyl)triacetic acid (NOTA), 1,4,7-triazacyclononane-1,4-diiacetic acid (NODA), N,N'-bis-[2-hydroxy-5-(carboxyethyl)benzyl]ethylenediamine-N,N'-diacetic acid (HBED-CC), 3,6,9,15-tetraazabicyclo[9.3.1]pentadeca-1(15), 11,13-triene-3,6,9,-triacetic acid (PCTA), diethylenetriaminepentaacetic acid (DTPA), N'-{5-[acetyl(hydroxy)amino]pentyl}-N-[5-({4-[(5-aminopentyl)(hydroxy)amino]-4-oxobutanoyl}amino) pentyl]-N-hydroxysuccinamide (DFO), 1,4,8,11-tetraazacyclododecane-1,4,8,11-tetraacetic acid (TETA), ethylenediamine-N,N'-tetraacetic acid (EDTA), 1,4,7-triazacyclononane-N-glutaric acid-N',N"-diacetic acid (NODAGA), 1,4,7-triazacyclononane-1-succinic acid-4,7-diacetic acid (NODASA), 1,4,7,10 tetraazacyclotridecane-1,4,7,10-tetraacetic acid (TRITA), trans-1,2-diaminocyclohexane-N,N,N',N'-tetraacetic acid (CDTA), 1-[2-(2-mercapto-2-methyl-propylamino)-ethylamino]-2-methyl-propane-2-thiol (BAT), 6-hydrazino-nicotinic acid (HYNIC), 1,4,7-triazacyclononane-1,4-bis[methylene(hydroxymethyl)phosphinic acid]-7-[methylene(2-carboxyethyl)phosphinic acid] and 1,4,7-triazacyclononane phosphinic acid.

These chelator groups may be attached to the linker groups in any manner. For example, the chelator group may be attached to a linker group via a nitrogen atom within a heterocyclic ring or chain of the chelator group or via a carboxylic acid in one of the side chains of the chelator group.

Certain chelator groups may be described by the following partial formula

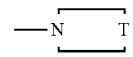

wherein T is —[$(CR^5_2)_m(NR^6)]_q(CR^5_2)_m$—.

Although a bond is depicted at the nitrogen atom in the ring, such chelator groups can also be bound to the remainder of the compound of formula (I) via other groups of the chelator group, such as via the side chains.

Each $R^5$ is independently selected from -hydrogen, -halogen, —OH, —$C_{1-6}$ alkyl and —O—$C_{1-6}$ alkyl. Preferably, each $R^5$ is -hydrogen.

Each $R^6$ is independently selected from -hydrogen, —$C_{1-6}$ alkyl, —($C_{1-6}$ alkylene)-COOH, —($C_{1-3}$ alkylene)-P(O)(OH)—($C_{1-3}$ alkylene)-COOH, and —($C_{1-3}$ alkylene)-P(O)(OH)—($C_{1-3}$ alkylene)-OH. Preferably, each $R^6$ is $C_3$ alkylene-COOH.

Each m is independently an integer from 1 to 4. Preferably, each m is 2 or 3.

q is an integer from 3 to 5. Preferably, q is 3.

The Radionuclide

Radionuclides are isotopes of elements of the periodic table which are considered unstable.

The nucleus of such radionuclides generally emits electromagnetic radiation, e.g. γ-radiation, or small particles, e.g. α- or β-radiation. In the present invention, radionuclides are preferably isotopes of elements of the periodic table which have a half-life of less than $10^{22}$ years, more preferably less than $10^{10}$ years, even more preferably less than $10^5$ years, even more preferably less than 100 years, most preferably less than 1 year. Some preferred radionuclides have a half-life of less than one week.

In the present invention the radionuclide is preferably selected from F-18, P-32, P-33, Sc-44, Sc-47, Cr-51, Fe-52, Fe-59, Mn-51, Mn-52m, Co-55, Co-57, Co-58, Cu-62, Cu-64, Cu-67, Ga-67, Ga-68, As-72, Se-75, As-77, Br-76, Br-75, Br-77, Br-80m, Br-82, Rb-82m, Sr-83, Sr-89, Y-86, Y-90, Zr-89, Mo-99, Tc-94m, Tc-99m, Ru-97, Rh-103m, Rh-105, Pd-109, Pt-109, Ag-111, In-110, In-111, In-113m, In-114m, Sb-119, Sn-121, Te-127, I-120, I-123, I-124, I-125, I-129, I-131, Pr-142, Pr-143, Pm-149, Pm-151, Sm-153, Dy-152, Dy-166, Gd-157, Gd-159, Ho-161, Tb-161, Ho-166, Er-169, Tm-172, Yb-169, Yb-175, Lu-177, Lu-177m, Re-186, Re-188, Re-189, Rd-188, Os-189m, Ir-192, Ir-194, Au-198, Au-199, Hg-197, Tl-201, Pb-203, Pb-211, Pb-212, Bi-211, Bi-212, Bi-213, At-211, At-217, Po-215, Ra-223, Rn-219, Fr-221, Ac-225, Th-227 and Fm-255.

More preferably, the radionuclide is selected from P-32, P-33, Sc-44, Sc-47, Co-58, Fe-59, Cu-64, Cu-67, Ga-67, Ga-68, Se-75, As-77, Br-80m, Sr-89, Zr-89, Y-90, Mo-99, Rh-103m, Rh-105, Pd-109, Pt-109, Ag-111, In-111, Sb-119, Sn-121, I-123, I-125, I-129, I-131, Te-127, Pr-142, Pr-143, Pm-149, Pm-151, Dy-152, Dy-166, Sm-153, Gd-159, Tb-161, Ho-161, Ho-166, Er-169, Tm-172, Yb-169, Yb-175, Lu-177, Lu-177m, Re-186, Re-188, Rd-188, Re-189, Os-189m, Ir-192, Ir-194, Au-198, Au-199, At-211, Pb-211, Pb-212, Bi-211, Bi-212, Bi-213, Po-215, At-217, Rn-219, Ra-223, Fr-221, Ac-225, Th-227 and Fm-255.

Even more preferably, the radionuclide is selected from Lu-177, Y-90, Cu-64, Ga-67, Ga-68, Sc-44, Zr-89 and In-111.

In the present invention, the radionuclide is usually reacted with the compound of formula (I) in the form of a salt of the radionuclide. These salts include an ion of the radionuclide and at least one further ion. If the radionuclide is a cation, one of the other ions is an anion, which may, e.g., be selected from acetate, bicarbonate, bromide, carbonate, chlorate, chloride, dihydrogen phosphate, fluoride, hydrogen phosphate, hydrogen sulfate, hydroxide, iodide, nitrate, nitride, nitrite, phosphate, sulfate, sulfide and sulfite. If the radionuclide is an anion, one of the other ions is a cation, which may, e.g., be selected from ammonium, lithium, sodium, magnesium, aluminum, potassium, calcium and gallium. Examples of such salts include $Lu(NO_3)_3$, $Y(NO_3)_3$, $Cu(NO_3)_2$, $Ga(NO_3)_3$, $Zr(NO_3)_4$, $In(NO_3)_3$, $LuCl_3$, $YCl_3$, $CuCl_2$, $GaC_3$, $ZrCl_4$ and $InCl_3$.

Processes for Preparing Compounds of Formula (I) without the Radionuclide

Compounds of the present application having structure C can be prepared by the reaction of a compound A with an activated derivative of a chelator B in the presence of a solvent and a base. Examples of activated derivatives of the carboxyl group in typical acylation reactions are described in the literature in the standard works, such as Houben-Weyl, Methoden der organischen Chemie [Methods of Organic Chemistry], Georg-Thieme-Verlag, Stuttgart). Activated esters can be formed in situ, for example by addition of HOBt (1-hydroxybenzotriazole) or N-hydroxysuccinimide.

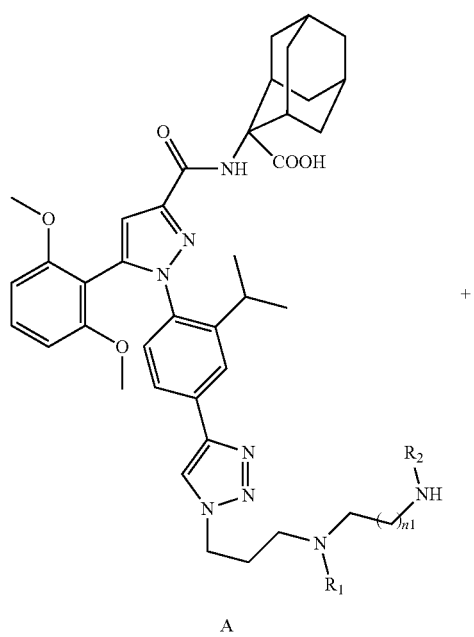

A

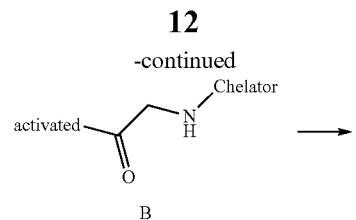

B

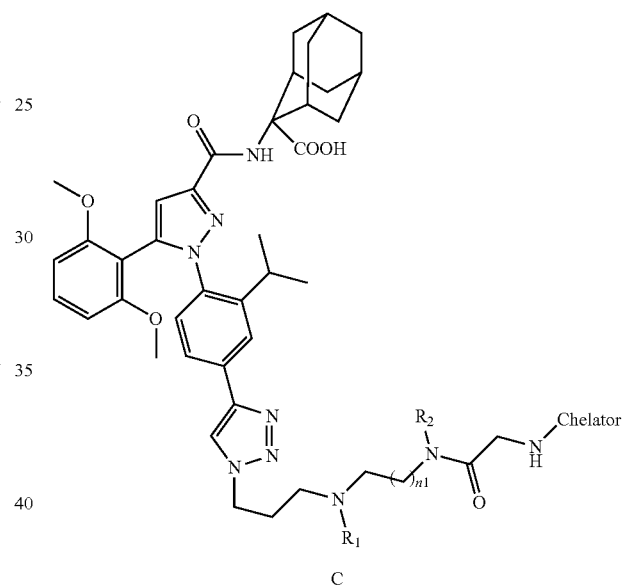

C

Preferred solvents are chosen from the group of dioxane, tetrahydrofuran, dimethylformamide and acetonitrile. The reaction is usually carried out under inert atmosphere. Preferred bases are chosen from triethylamine and diisopropylethylamine. The reaction can be carried out in a temperature range from 20° C. to 90° C., preferably at 30° C., for a duration in the range from 1 to 48 h, preferably 24 h. The group shown as "activated" can be O-succinimide, acid-halogenide or acid-anhydride. The variable n1 is from 1 to 10.

Compounds of structure F can be prepared by the reaction of a compound D with an azide derived chelator E in the presence of a solvent, a copper source and a reductant.

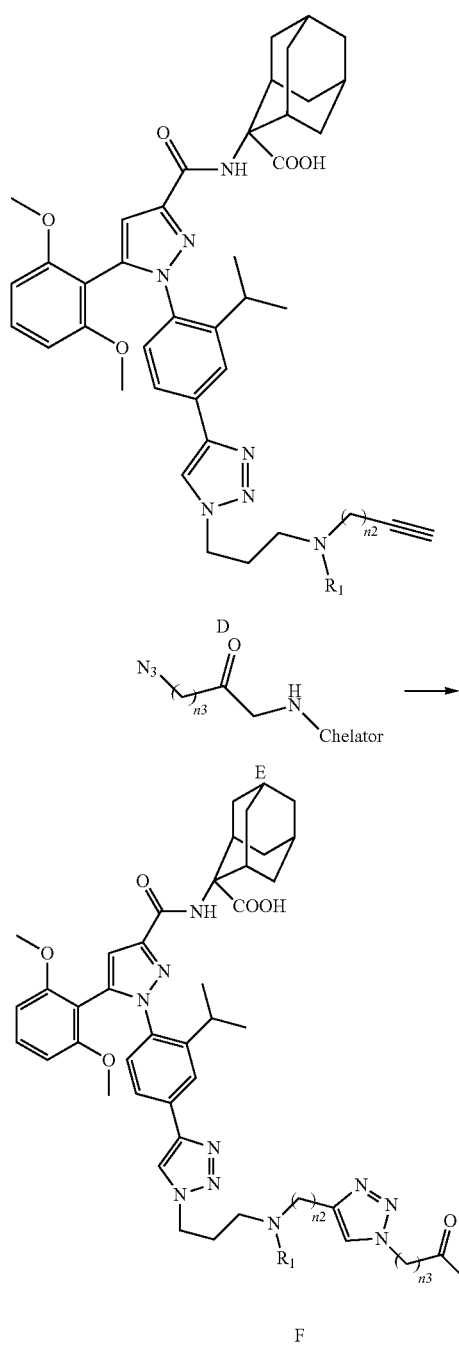

D

E

F

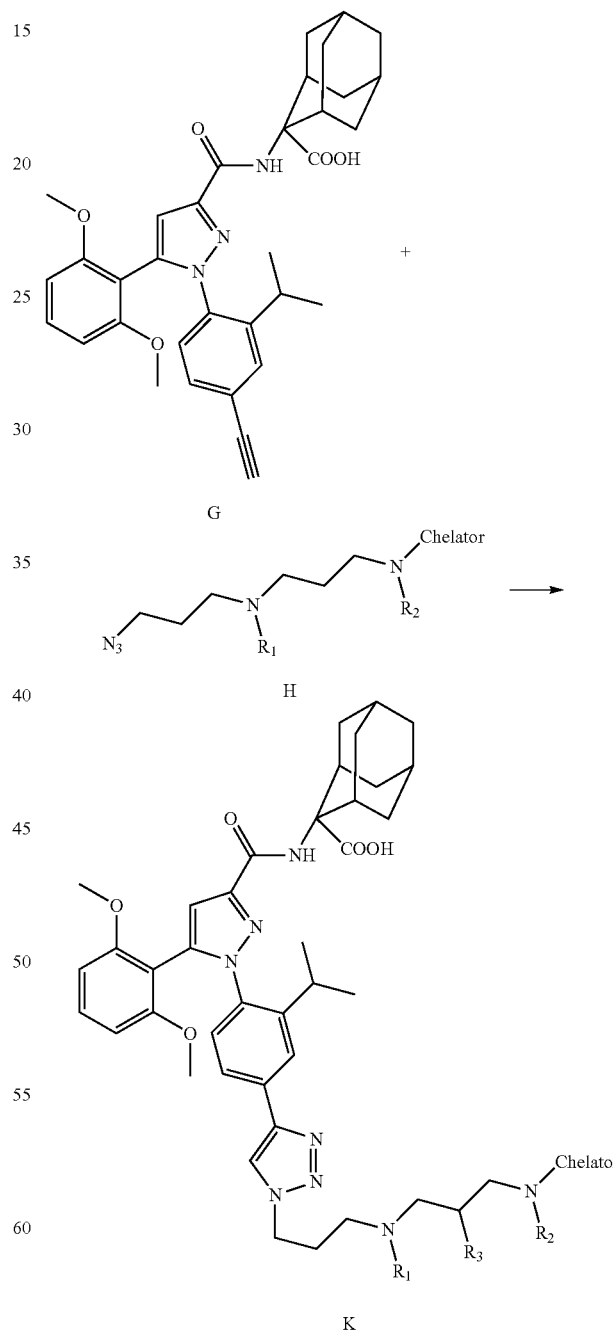

G

H

K

Assisted Aminocarbonylation, Christopher Lang and Peter Gmeiner, Synthesis (2013); and ""Click" chemistry toward bis (DOTA-derived) heterometallic complexes: potential bimodal MRI/PET (SPECT) molecular imaging probes." Suchý, Mojmfr, Robert Bartha, and Robert H E Hudson, RSC Advances 3, 10 (2013): 3249-3259; For a recent review on CuAAC chemistry applied to metal chelating systems see: H. Struthers, T. L. Mindt and R. Schibli, *Dalton Trans.*, 2010, 39, 675).

Compounds of the structure K can be prepared by the reaction of a compound G with an azide derived chelator H in the presence of a solvent, a copper source and a reductant.

Preferred solvents are chosen from the group of tetrahydrofuran, dimethylformamide and t-butanol with or without addition of water. The reaction is typically carried out under inert atmosphere and a copper source such as $CuSO_4$, CuI, copper on charcoal, or $Cu(OAc)_2$ is added. The reaction is carried out in presence or absence of a reductant which is preferably ascorbic acid. Reaction temperatures vary in a range from 20° C. to 90° C., preferably 25° C. to 35° C. Typical reaction durations are in the range from 1-48 h, preferably about 24 h. The variables n2 and n3 are independently from 1 to 10.

Compounds of structures D and E can be obtained according to literature procedures (Efficient Synthesis of Heterocyclic Neurotensin Receptor Ligands by Microwave Preferred solvents are chosen from the group of tetrahydrofuran, dimethylformamide and t-butanol with or without addition of water. The reaction is typically carried out under inert atmosphere and a copper source, which may be chosen from the group $CuSO_4$, CuI, copper on charcoal, $Cu(OAc)_2$, is typically added. The reaction is carried out in presence or absence of a reductant which is preferably ascorbic acid. Reaction temperatures are usually in the range from 20° C. to 90° C., preferably 25° C. to 35° C. Typical reaction durations are in the range from 1-48 h, preferably 24 h.

Further examples of reactions which may be used for preparing compounds of formula (G) are described in non-patent document 11 and in "Efficient Synthesis of Heterocyclic Neurotensin Receptor Ligands by Microwave Assisted Aminocarbonylation" by Lang, C. and Gmeiner, P., Synthesis 2013, 45, 2474-2480).

The Sonagashira reaction has been reviewed in "A Booming Methodology in Synthetic organic Chemistry" by Chinchilla, R. and Najera, C. in Chem. Rev., 2007, 107 (3), 874-922.

Processes for Reacting Compounds of Formula (I) with a Radionuclide

The present invention further relates to a process comprising reacting a compound of formula (I) according to the present invention with one or more diagnostically or therapeutically effective radionuclides to provide a complex of the compound of formula (I) with the one or more diagnostically or therapeutically effective radionuclides.

This reaction is preferably carried out in a solvent comprising water which may further comprise a buffer. The buffer is preferably 4-(2-hydroxyethyl)-1-piperazineethanesulfonic acid or sodium acetate.

In the process according to the present invention, the pH of the solution in which the reaction is carried out is preferably in the range from 2 to 7, more preferably 4 to 6 and most preferably 4.5 to 5.5. Moreover, the reaction is preferably carried out at a temperature in the range from 20° C. to 100° C., more preferably from 50° C. to 98° C. and most preferably from 85° C. to 95° C.

The reaction is preferably carried out for a duration of from 5 to 30 minutes, more preferably 7 to 15 minutes, most preferably 8 to 12 minutes.

Synthesis of this type have been reported in literature ("Syntheses, Receptor Bindings, in vitro and in vivo Stabilities and Biodistributions of DOTA-Neurotensin(8-13) Derivatives Containing Beta-Amino Acid Residues—A Lesson about the Importance of Animal Experiments" by Sparr, Christof; Purkayastha, Nirupam; Yoshinari, Tomohiro; Seebach, Dieter; Maschauer, Simone; Prante, Olaf; Hubner, Harald; Gmeiner, Peter; Kolesinska, Beata; Cescato, Renzo; Waser, Beatrice; and Claude Reubi, Jean; Biodiversity 2013, 10, 2101-212; "$^{18}$F- and $^{68}$Ga-labeled Neurotensin Peptides for PET Imaging of Neurotensin Receptor 1" by Maschauer, Simone; Einsiedel, Juergen; Hübner, Harald; Gmeiner, Peter; and Prante. Olaf; J. Med. Chem. 2016, in press)

Furthermore, similar reactions have been summarized in a number of reviews (Brasse, David, and Aline Nonat; "Radiometals: towards a new success story in nuclear imaging?"; Dalton Transactions 44.11 (2015): 4845-4858; Cai, Zhengxin, and Anderson, C. J.; "Chelators for copper radionuclides in positron emission tomography radiopharmaceuticals"; Journal of Labelled Compounds and Radiopharmaceuticals 57.4 (2014): 224-230; Deri, Melissa A., et al.; "PET imaging with $^{89}$Zr: from radiochemistry to the clinic"; Nuclear Medicine and Biology 40.1 (2013): 3-14; Price, Eric W., and Orvig, C.; "Matching chelators to radiometals for radiopharmaceuticals"; Chemical Society Reviews 43.1 (2014): 260-290).

Compositions, Complexes and Kits

The present invention further relates to a complex obtainable by the process of the present invention, optionally in the form of a pharmaceutically acceptable salt, solvate, ester, polymorph, tautomer, racemate, enantiomer, or diastereomer or mixture thereof.

In the complexes of the present invention, at least one type of radionuclide is bound to and/or complexed with the compound of formula (I). Such binding and/or complexing is typically achieved by an interaction between the chelator group and the radionuclide.

The present invention further relates to a composition or complex comprising the compound according to the present invention, optionally in the form of a pharmaceutically acceptable salt, solvate, ester, polymorph, tautomer, racemate, enantiomer, or diastereomer or mixture thereof, and one or more diagnostically or therapeutically effective radionuclides.

The present invention also relates to a pharmaceutical composition, wherein the composition comprises (i) a compound, composition or complex of the present invention and optionally (ii) a pharmaceutically acceptable excipient.

Pharmaceutically acceptable excipients for use in the pharmaceutical composition comprise one or more bulking agents, carriers, diluents, fillers, disintegrants, lubricating agents, binders, colorants, pigments, stabilizers, preservatives, antioxidants, and/or solubility enhancers. Preferred excipients are antioxidants and solubility enhancers.

The diluent is preferably the buffer to be used for injection, which can, e.g., be a phosphate buffer. Furthermore, the diluent may include saccharides, including monosaccharides, disaccharides, polysaccharides and sugar alcohols such as arabinose, lactose, dextrose, sucrose, fructose, maltose, mannitol, erythritol, sorbitol, xylitol lactitol, and derivatives thereof.

Injectionable solutions of the compounds, compositions and complexes of the present invention can be formulated in saline or isotonic buffers, e.g., with a maximum ethanol content of 10%. A preferred example of a stabilizer is gentisinic acid (2,5-dihydroxybenzoic acid). Sodium ascorbate is preferably added as an antioxidant.

The present invention also provides kits comprising a compound of formula (I) and one or more radionuclides. Examples of radionuclides are described above.

Disorders which May be Treated, Diagnosed or Prevented by Compounds of the Present Invention The present invention also relates to the use of the compounds, compositions or complexes described herein in medicine, in particular for the use in diagnosis, treatment or prevention of a disorder.

A large variety of disorders may be diagnosed, treated or prevented with the compounds of the present invention, comprising tumors and hematological malignancies. Preferred are disorders involving a neurotensin receptor. More preferably, the disorder is a disorder involving neurotensin receptor 1.

Specific examples of cancer-related disorders are prostate cancer, lung cancer, thyroid cancer, pancreatic cancer, colon cancer, rectal cancer, pituitary cancer and breast cancer.

When the compounds of the present invention are provided in crystalline form, the structure can contain solvent molecules. The solvents are typically pharmaceutically acceptable solvents and include, among others, water (hydrates) or organic solvents. Examples of possible solvates include ethanolates and iso-propanolates.

Moreover, the scope of the invention embraces the compounds of formula (I) in any solvated form, including, e.g., solvates with water, for example hydrates, or with organic solvents such as, e.g., methanol, ethanol or acetonitrile, i.e., as a methanolate, ethanolate or acetonitrilate, respectively, or in the form of any polymorph. It is to be understood that such solvates of the compounds of the formula (I) also include solvates of pharmaceutically acceptable salts of the compounds of the formula (I).

Furthermore, the compounds of formula (I) may exist in the form of different isomers, in particular stereoisomers (including, e.g., geometric isomers (or cis/trans isomers), enantiomers and diastereomers) or tautomers. All such isomers of the compounds of formula (I) are contemplated as being part of the present invention, either in admixture or in pure or substantially pure form. As for stereoisomers, the invention embraces the isolated optical isomers of the compounds according to the invention as well as any mixtures thereof (including, in particular, racemic mixtures/racemates). The racemates can be resolved by physical methods, such as, e.g., fractional crystallization, separation or crystallization of diastereomeric derivatives, or separation by chiral column chromatography. The individual optical isomers can also be obtained from the racemates via salt formation with an optically active acid followed by crystallization. The present invention further encompasses any tautomers of the compounds provided herein.

The scope of the invention also embraces compounds of formula (I), in which one or more atoms are replaced by a specific isotope of the corresponding atom. For example, the invention encompasses compounds of formula (I), in which one or more hydrogen atoms (or, e.g., all hydrogen atoms) are replaced by deuterium atoms (i.e., $^2$H; also referred to as "D").

The compounds provided herein may be administered as compounds per se or may be formulated as medicaments. The medicaments/pharmaceutical compositions may optionally comprise one or more pharmaceutically acceptable excipients, such as carriers, diluents, fillers, disintegrants, lubricating agents, binders, colorants, pigments, stabilizers, preservatives, antioxidants, and/or solubility enhancers.

Furthermore, the compounds provided herein may be administered as a single dose administration or, preferably, a multiple-dose administration.

In particular, the pharmaceutical compositions may comprise one or more solubility enhancers, such as, e.g., poly(ethylene glycol), including poly(ethylene glycol) having a molecular weight in the range of about 200 to about 5,000 Da, ethylene glycol, propylene glycol, non-ionic surfactants, tyloxapol, polysorbate 80, macrogol-15-hydroxystearate, phospholipids, lecithin, dimyristoyl phosphatidylcholine, dipalmitoyl phosphatidylcholine, distearoyl phosphatidylcholine, cyclodextrins, α-cyclodextrin, β-cyclodextrin, γ-cyclodextrin, hydroxyethyl-β-cyclodextrin, hydroxypropyl-β-cyclodextrin, hydroxyethyl-γ-cyclodextrin, hydroxypropyl-γ-cyclodextrin, dihydroxypropyl-β-cyclodextrin, sulfobutylether-β-cyclodextrin, sulfobutylether-γ-cyclodextrin, glucosyl-α-cyclodextrin, glucosyl-β-cyclodextrin, diglucosyl-β-cyclodextrin, maltosyl-α-cyclodextrin, maltosyl-β-cyclodextrin, maltosyl-γ-cyclodextrin, maltotriosyl-β-cyclodextrin, maltotriosyl-γ-cyclodextrin, dimaltosyl-β-cyclodextrin, methyl-β-cyclodextrin, carboxyalkyl thioethers, hydroxypropyl methylcellulose, hydroxypropylcellulose, polyvinylpyrrolidone, vinyl acetate copolymers, vinyl pyrrolidone, sodium lauryl sulfate, dioctyl sodium sulfosuccinate, or any combination thereof.

The pharmaceutical compositions can be formulated by techniques known to the person skilled in the art, such as the techniques published in "Remington: The Science and Practice of Pharmacy", Pharmaceutical Press, $22^{nd}$ edition.

The compounds of formula (I) or the above described pharmaceutical compositions comprising a compound of formula (I) may be administered to a subject by any convenient route of administration, whether systemically/peripherally or at the site of desired action. Parenteral administration is preferred. This includes, e.g., using injection techniques or infusion techniques, and including, for example, by injection, e.g., subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, or intrasternal, most preferably intravenous injection.

If the compounds or pharmaceutical compositions are administered parenterally, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard (radio)pharmaceutical techniques well known to those skilled in the art.

In this specification, a number of documents including patent applications and scientific literature are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The present invention can be summarized in the following items 1 to 36:

(1) A compound of formula (I), optionally in the form of a pharmaceutically acceptable salt, solvate, ester, polymorph, tautomer, racemate, enantiomer, diastereomer or mixture thereof

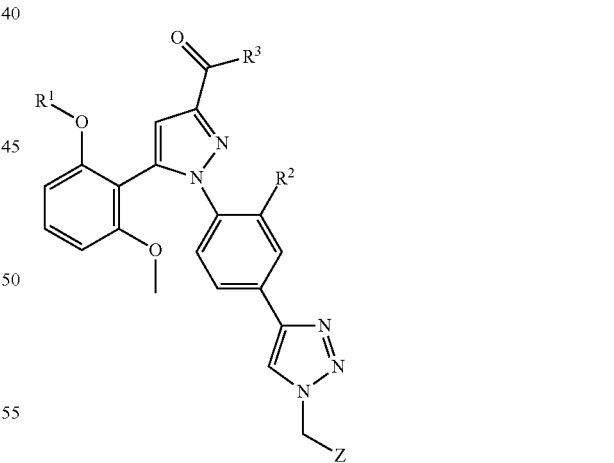

wherein $R^1$ is selected from the group consisting of -hydrogen, —($C_{1-6}$ alkyl), —($C_{3-6}$ cycloalkyl) and —($C_{1-3}$ alkylene-$C_{3-6}$ cycloalkyl), wherein $C_{1-6}$ alkyl, $C_{3-6}$ cycloalkyl and the $C_{1-3}$ alkylene and $C_{3-6}$ cycloalkyl in ($C_{1-3}$ alkylene-$C_{3-6}$ cycloalkyl) may be substituted with one or more halogen atoms, $R^2$ is selected from -hydrogen, -halogen, nitro, —($C_{1-6}$ alkyl), —($C_{3-6}$ cycloalkyl) and —($C_{1-3}$ alkylene-$C_{3-6}$ cycloalkyl), wherein $C_{1-6}$ alkyl, $C_{3-6}$ cycloalkyl and the $C_{1-3}$ alkylene and $C_{3-6}$ cycloalkyl in ($C_{1-3}$ alkylene-$C_{3-6}$ cycloalkyl) may be substituted with one or more halogen atoms, $R^3$ is selected from 2-amino-2-adamantane carboxylic acid, cyclohexylglycine and 9-amino-bicyclo[3.3.1]nonane-9-carboxylic acid, and Z comprises a chelator group.

(2) The compound of formula (I) according to item 1, wherein $R^1$ is —($C_{1-3}$ alkyl).

(3) The compound of formula (I) according to item 1 or 2, wherein $R^2$ is —($C_{1-6}$ alkyl).

(4) The compound of formula (I) according to any one of items 1 to 3, wherein $R^3$ is

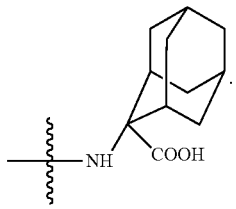 [SMILES: *NC1(C(=O)O)C2CC3CC(C2)CC1C3]

(5) The compound of formula (I) according to any one of items 1 to 4, wherein the chelator group is -(hydrocarbon group which contains from 8 to 40 carbon atoms, 2 to 12 nitrogen atoms and optionally 1 to 10 oxygen atoms and/or optionally 1 to 5 sulfur atoms and/or optionally 1 to 5 phosphor atoms).

(6) The compound of formula (I) according to any one of items 1 to 5, wherein the chelator group comprises at least two groups selected from carboxylic acid, phosphinic acid, phosphonic acid and hydroxylamine.

(7) The compound of formula (I) according to any one of items 1 to 6, wherein group Z comprises one or two or three groups of the following partial structure,

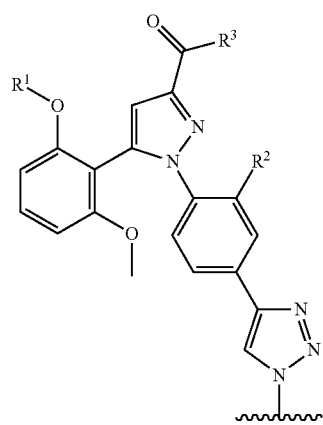

wherein the definitions of $R^1$, $R^2$ and $R^3$ are independently as defined in any one of items 1 to 5.

(8) The compound of formula (I) according to any one of items 1 to 7, wherein the chelator group is selected from 1,4,7,10-tetraazacyclododecane-1,4,7,10-tetraacetic acid (DOTA), 2,2',2''-(1,4,7-triazonane-1,4,7-triyl)triacetic acid (NOTA), 1,4,7-triazacyclononane-1,4-diiacetic acid (NODA), N,N'-bis-[2-hydroxy-5-(carboxyethyl)benzyl]ethylenediamine-N,N'-diacetic acid (HBED-CC), 3,6,9,15-tetraazabicyclo[9.3.1]pentadeca-1(15), 11,13-triene-3, 6,9,-triacetic acid (PCTA), diethylenetriaminepentaacetic acid (DTPA), N'-{5-[acetyl(hydroxy)amino]pentyl}-N-[5-({4-[(5-aminopentyl)(hydroxy)amino]-4-oxobutanoyl}amino)pentyl]-N-hydroxy-succinamide (DFO), 1,4,8,11-tetraazacyclododecane-1,4,8,11-tetraacetic acid (TETA), ethylenediamine-N,N'-tetraacetic acid (EDTA), 1,4,7-triazacyclononane-N-glutaric acid-N',N''-diacetic acid (NODAGA), 1,4,7-triazacyclononane-1-succinic acid-4,7-diacetic acid (NODASA), 1,4,7,10 tetraazacycotridecane-1,4,7,10-tetraacetic acid (TRITA), trans-1,2-diaminocyclohexane-N, N,N',N'-tetraacetic acid (CDTA), 1-[2-(2-mercapto-2-methyl-propylamino)-ethylamino]-2-methyl-propane-2-thiol (BAT), 6-Hydrazino-nicotinic acid (HYNIC), 1,4,7-triazacyclononane-1,4-bis[methylene(hydroxymethyl) phosphinic acid]-7-[methylene(2-carboxyethyl) phosphinic acid] and 1,4,7-triazacyclononane phosphinic acid.

(9) The compound of formula (I) according to any one of items 1 to 7, wherein the chelator group is

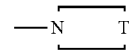

wherein T is —[$(CR^5_2)_m(NR^6)]_q(CR^5_2)_m$—
wherein
each $R^5$ is independently selected from -hydrogen, -halogen, —OH, —$C_{1-6}$ alkyl and —O—$C_{1-6}$ alkyl,
each $R^6$ is independently selected from -hydrogen, —$C_{1-6}$ alkyl, —($C_{1-6}$ alkylene)-COOH, —($C_{1-3}$ alkylene)-P(O)(OH)—($C_{1-3}$ alkylene)-COOH, —($C_{1-3}$ alkylene)-P(O)(OH)—($C_{1-3}$ alkylene)-OH,
each m is independently an integer from 1 to 4, and
q is an integer from 3 to 5.

(10) The compound of formula (I) according to item 9, wherein each $R^5$ is -hydrogen.

(11) The compound of formula (I) according to item 9 or 10, wherein each $R^6$ is $C_{1-3}$ alkyl-COOH.

(12) The compound of formula (I) according to any one of items 9 to 11, wherein each m is 2 or 3.

(13) The compound of formula (I) according to any one of items 9 to 12, wherein q is 3.

(14) The compound of formula (I) according to any one of items 1 to 13, wherein Z is -(linker group)-(chelator group) and the
linker group is —(X)$_p$—, wherein
p is an integer from 1 to 10, and
each X is independently selected from
(a) —(N($R^4$)—$C_{1-10}$ alkylene)-,
(b) —(N($R^4$)-heteroarylene)-,
(c) —(N($R^4$)—C(O))—,
(d) —(O—$C_{1-10}$ alkylene)-,
(e) —(O-heteroarylene)-,
(f) —(O—C(O))—,
(g) —($C_{1-10}$ alkylene-heteroarylene)-,
(h) —($C_{1-10}$ alkylene-C(O))—,
(i) —(C(O)—$C_{1-10}$ alkylene)-,
(j) —(C(O)-heteroarylene)-,
(k) —(heteroarylene-$C_{1-10}$ alkylene)-,
(l) —(heteroarylene-C(O))—, and
(m) —($C_{1-10}$ alkylene)-,
wherein each $C_{1-10}$ alkylene is independently optionally substituted with one or more selected from halogen, C(O)OH and OH, wherein heteroarylene is 4 to 6-membered heteroarylene comprising 1 to 3 heteroatoms selected from N, O and S and wherein the heteroarylene is optionally substituted with one or more selected from halogen and $C_{1-6}$ alkyl; and wherein each $R^4$ is independently selected from hydrogen and $C_{1-6}$ alkyl.

(15) The compound of formula (I) according to item 14, wherein p is an integer from 1 to 5.

(16) The compound of formula (I) according to item 14 or 15, wherein the linker group is selected from (i) —$C_{1-10}$ alkylene-N($R^4$)—$C_{1-10}$ alkylene-N($R^4$)—C(O)—$C_{1-10}$ alkylene-N($R^4$)—, (ii) —$C_{1-10}$ alkylene-N($R^4$)—$C_{1-10}$ alkylene-heteroarylene-$C_{1-10}$ alkylene-C(O)—$C_{1-10}$ alkylene-N($R^4$)—, and (iii) —$C_{1-10}$ alkylene-N($R^4$)—$C_{1-10}$ alkylene-N($R^4$)—.

wherein each $C_{1-10}$ alkylene is independently optionally substituted with one or more selected from halogen, C(O)OH and OH, and wherein heteroarylene is 4 to 6-membered heteroarylene comprising 1 to 3 heteroatoms selected from N, O and S and wherein the heteroarylene is optionally substituted with one or more selected from halogen and $C_{1-6}$ alkyl, and wherein each $R^4$ is independently selected from hydrogen and $C_{1-6}$ alkyl.

(17) The compound of formula (I) according to any one of items 14 to 16, wherein each $R^4$ is independently selected from H, methyl, ethyl, n-propyl and iso-propyl.

(18) A composition or complex comprising the compound according to any one of items 1 to 17, optionally in the form of a pharmaceutically acceptable salt, solvate, ester, polymorph, tautomer, racemate, enantiomer, or diastereomer or mixture thereof, and one or more diagnostically or therapeutically effective radionuclides.

(19) The composition or complex according to item 18, wherein the radionuclide is selected from F-18, P-32, P-33, Sc-44, Sc-47, Cr-51, Fe-52, Fe-59, Mn-51, Mn-52m, Co-55, Co-57, Co-58, Cu-62, Cu-64, Cu-67, Ga-67, Ga-68, As-72, Se-75, As-77, Br-76, Br-75, Br-77, Br-80m, Br-82, Rb-82m, Sr-83, Sr-89, Y-86, Y-90, Zr-89, Mo-99, Tc-94m, Tc-99m, Ru-97, Rh-103m, Rh-105, Pd-109, Pt-109, Ag-111, In-110, In-111, In-113m, In-114m, Sb-119, Sn-121, Te-127, I-120, I-123, I-124, I-125, I-129, I-131, Pr-142, Pr-143, Pm-149, Pm-151, Sm-153, Dy-152, Dy-166, Gd-157, Gd-159, Ho-161, Tb-161, Ho-166, Er-169, Tm-172, Yb-169, Yb-175, Lu-177, Lu-177m, Re-186, Re-188, Re-189, Rd-188, Os-189m, Ir-192, Ir-194, Au-198, Au-199, Hg-197, Tl-201, Pb-203, Pb-211, Pb-212, Bi-211, Bi-212, Bi-213, At-211, At-217, Po-215, Ra-223, Rn-219, Fr-221, Ac-225, Th-227 and Fm-255.

(20) The composition or complex according to item 18, wherein the radionuclide is selected from P-32, P-33, Sc-44, Sc-47, Co-58, Fe-59, Cu-64, Cu-67, Ga-67, Ga-68, Se-75, As-77, Br-80m, Sr-89, Zr-89, Y-90, Mo-99, Rh-103m, Rh-105, Pd-109, Pt-109, Ag-111, In-111, Sb-119, Sn-121, I-123, I-125, I-129, I-131, Te-127, Pr-142, Pr-143, Pm-149, Pm-151, Dy-152, Dy-166, Sm-153, Gd-159, Tb-161, Ho-161, Ho-166, Er-169, Tm-172, Yb-169, Yb-175, Lu-177, Lu-177m, Re-186, Re-188, Rd-188, Re-189, Os-189m, Ir-192, Ir-194, Au-198, Au-199, At-211, Pb-211, Pb-212, Bi-211, Bi-212, Bi-213, Po-215, At-217, Rn-219, Ra-223, Fr-221, Ac-225, Th-227 and Fm-255.

(21) The composition or complex according to item 18, wherein the radionuclide is selected from Lu-177, Y-90, Cu-64, Ga-67, Ga-68, Sc-44, Zr-89 and In-111.

(22) A process comprising reacting a compound of formula (I) according to any one of items 1 to 17 with one or more diagnostically or therapeutically effective radionuclides to provide a complex of the compound of formula (I) with the one or more diagnostically or therapeutically effective radionuclides.

(23) The process according to item 22, wherein the reaction is carried out in a solvent comprising water.

(24) The process according to item 23, wherein the water further comprises a buffer.

(25) The process according to item 24, wherein the buffer is 4-(2-hydroxyethyl)-1-piperazineethanesulfonic acid or sodium acetate.

(26) The process according to any one of items 22 to 25, wherein the pH of the solution in which the reaction is carried out is in the range from 2 to 7, preferably 4 to 6, more preferably 4.5 to 5.5.

(27) The process according to any one of items 22 to 26, wherein the reaction is carried out at a temperature in the range from 20° C. to 100° C., preferably from 80 to 98° C. and more preferably from 85 to 95° C.

(28) The process according to any one of items 22 to 27, wherein the reaction is carried out for a duration of from 5 to 30 minutes, preferably 7 to 15 minutes, more preferably 8 to 12 minutes.

(29) A complex obtainable by the process of any one of items 22 to 28, optionally in the form of a pharmaceutically acceptable salt, solvate, ester, polymorph, tautomer, racemate, enantiomer, or diastereomer or mixture thereof.

(30) The compound according to any one of items 1 to 17 or the composition or complex according to items 18 to 21 or the complex according to item 29, for use in medicine.

(31) The compound according to any one of items 1 to 17 or the composition or complex according to items 18 to 21 or the complex according to item 29, for use in the diagnosis of a disorder.

(32) The compound according to any one of items 1 to 17 or the composition or complex according to items 18 to 21 or the complex according to item 29, for use in the treatment or prevention of a disorder.

(33) The compound, composition or complex for use according to item 31 or 32, wherein the disorder is a disorder involving neurotensin receptor, preferably, the disorder is a disorder involving neurotensin receptor 1.

(34) The compound, composition or complex for use according to item 31 or 32, wherein the disorder is selected from the group comprising tumors and hematological malignancies.

(35) The compound, composition or complex for use according to item 31 or 32, wherein the disorder is selected from the group consisting of prostate cancer, lung cancer, thyroid cancer, pancreatic cancer, colon cancer, rectal cancer, pituitary cancer and breast cancer.

(36) A method of diagnosing a disorder in which a diagnostically effective amount of a compound according to any one of items 1 to 17 or a diagnostically effective amount of a composition or a diagnostically effective amount of a complex according to items 18 to 21 or a diagnostically effective amount of a complex according to item 29 is administered to a patient in need thereof.

(37) A method of treating or preventing a disorder in which a therapeutically effective amount of a compound according to any one of items 1 to 17 or a therapeutically effective amount of a composition or a therapeutically effective amount of a complex according to items 18 to 21 or a therapeutically effective amount of a complex according to item 29 is administered to a patient in need thereof.

(38) The method according to item 36 or 37, wherein the disorder is a disorder involving neurotensin receptor, preferably, the disorder is a disorder involving neurotensin receptor 1.

(39) The method according to item 36 or 37, wherein the disorder is selected from the group comprising tumors and hematological malignancies.

(40) The method according to item 36 or 37, wherein the disorder is selected from the group consisting of prostate cancer, lung cancer, thyroid cancer, pancreatic cancer, colon cancer, rectal cancer, pituitary cancer and breast cancer.

(41) Use of a compound according to any one of items 1 to 17 or a composition or a complex according to items 18 to 21 or a complex according to item 29 for the preparation of an agent for diagnosing a disorder.

(42) Use of a compound according to any one of items 1 to 17 or a composition or a complex according to items 18 to 21 or a complex according to item 29 for the preparation of an agent for treating or preventing a disorder.

(43) The use according to item 41 or 42, wherein the disorder is a disorder involving neurotensin receptor, preferably, the disorder is a disorder involving neurotensin receptor 1.

(44) The use according to item 41 or 42, wherein the disorder is selected from the group comprising tumors and hematological malignancies.

(45) The use according to item 41 or 42, wherein the disorder is selected from the group consisting of prostate cancer, lung cancer, thyroid cancer, pancreatic cancer, colon cancer, rectal cancer, pituitary cancer and breast cancer.

(46) A pharmaceutical composition, wherein the composition comprises (i) a compound according to any one of items 1 to 17, or the composition or complex according to items 18 to 21 or the complex according to item 29 and optionally (ii) a pharmaceutically acceptable excipient.

(47) A kit comprising a compound according to any one of items 1 to 17 and one or more radionuclides.

Various modifications and variations of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

The following examples are merely illustrative of the present invention and should not be construed to limit the scope of the invention which is defined by the appended claims.

EXAMPLES

Figure 2:
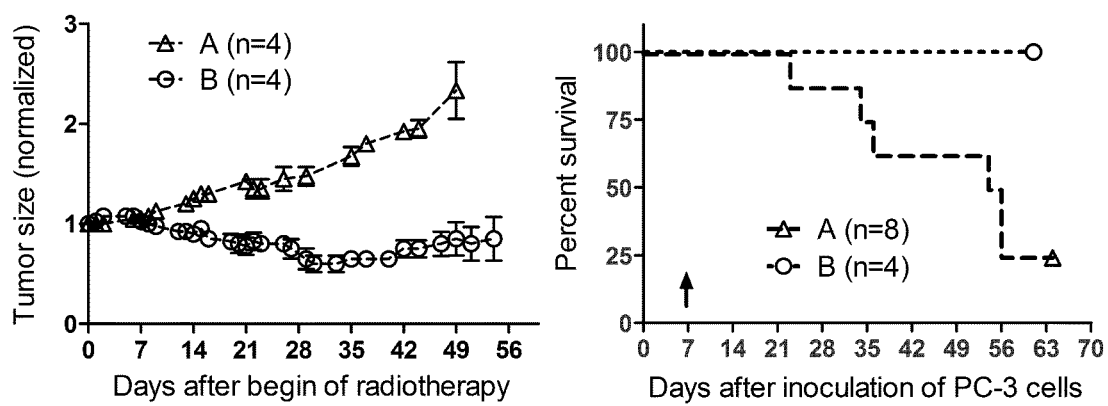
FIG. 2 shows results of the therapy study using PC3-xenografted nude mice injected either with $^{177}$Lu-14 (group B) or with saline (control, group A). Left: Progression of tumor size (tumor diameter) normalized to the day at begin of therapy. Right: Survival curves of $^{177}$Lu-14-treated animals in comparison with untreated control animals. The arrow indicates the begin of radiotherapy.

In the following, the synthesis of compounds according to the present invention, radiolabeling with Lu-177 and successful use in radiotherapy of prostate tumor in a mouse model is described. The results are also shown in FIGS. 1 and 2.

General Methods

All reactions requiring anhydrous conditions were carried out under nitrogen and the solvents were dried appropriately before use. All reactions were monitored by TLC using silica gel 60 $F_{254}$ plates. Visualization of the reaction components was achieved using UV fluorescence (254 nm) and $KMnO_4$ stain. Silica gel chromatography was carried out over Silicagel 60. The yields reported are after purification.

$^1H$ and $^{13}C$ NMR spectra were recorded in deuterated solvents and chemical shifts ($\delta$) are quoted in parts per million (ppm) calibrated to TMS ($^1H$ and $^{13}C$). Coupling constants (J) are measured in Hertz (Hz). The following abbreviations are used to describe multiplicities: s=singlet, d=doublet, t=triplet, q=quartet, b=broad, m=multiplet.

Purity and identity were assessed by analytical RP-HPLC (Agilent 1100 analytical series, column: Zorbax Eclipse XDB-C8 analytical column, 4.6×150 mm, 5 µm, flow rate: 0.5 ml/min, detection wavelength: 254 nm) coupled to a Bruker Esquire 2000 mass detector equipped with an ESI- or APCI-trap. Purities of the products were assessed from HPLC-MS.

System A: methanol/$H_2O$ 0.1% HCOOH as the solvent system and employing the following gradient system 0-3 min: 10% methanol, 3-18 min: 10-100% methanol, 18-24 min: 100% methanol, 24-30 min: 100-10% methanol, flow rate: 0.5 ml/min.

System B: methanol/$H_2O$ 0.1% HCOOH as the solvent system and employing the following gradient system in 0-11 min: 10-100% methanol, in 11-16 min: 100% methanol, 16-19 min: 100-10% methanol, flow rate: 0.5 ml/min.

System C: acetonitrile/$H_2O$ 0.1% TFA as the solvent system and employing the following gradient system in 0-21 min: 10-100% acetonitrile, 21-24 min: 100% acetonitrile, 24-27 min 100-10% acetonitrile.

System D: methanol/$H_2O$ 0.1% HCOOH as the solvent system and employing the following gradient system in 0-21 min: 10-100% methanol, in 21-24 min: 100% methanol, 24-27 min: 100-10% methanol, flow rate: 0.5 ml/min.

System E: methanol/$H_2O$ 0.1% HCOOH as the solvent system and employing the following gradient system in 0-12 min: 10-100% methanol, in 12-15 min: 100% methanol, 15-18 min: 100-10% methanol, flow rate: 0.5 ml/min.

Example 1

The product 14 of the following example was highly beneficial in comparison with previously published analogs such as described in WO 2014/086499. Without wishing to be bound by theory, it is assumed that this is due to the significantly improved selectivity to the NTS1 receptor with decreased affinity to dopamine receptors and due to its increased tumor growth inhibition rate in vivo.

25 26
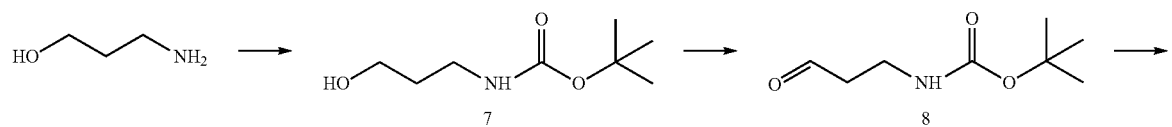
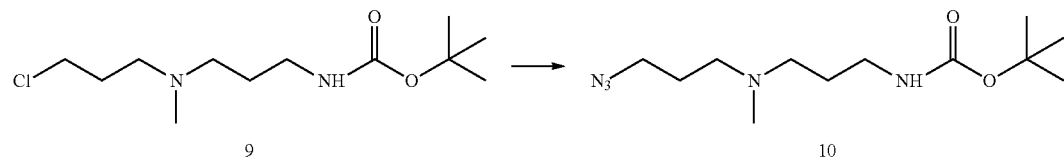
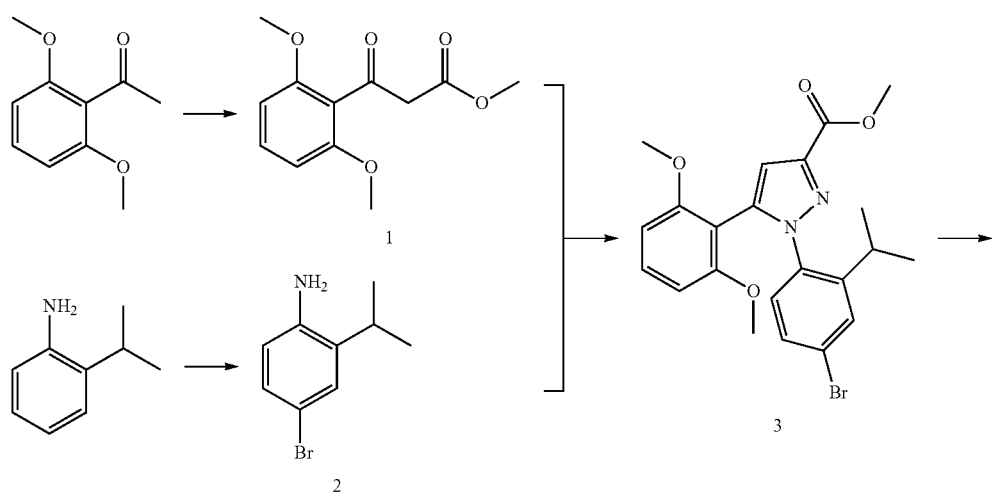
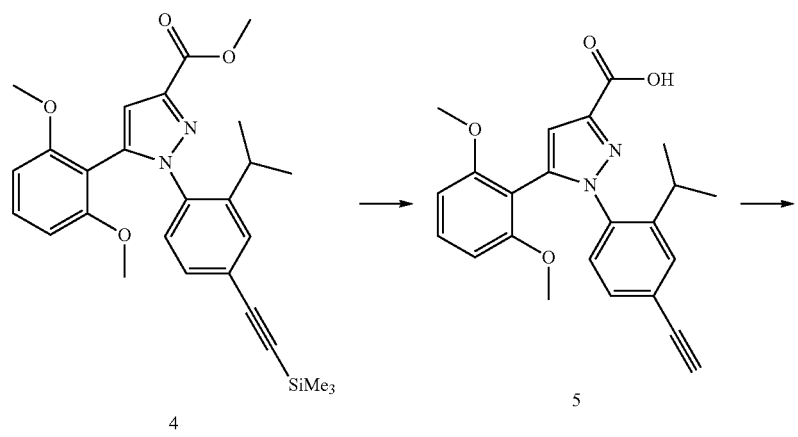

-continued
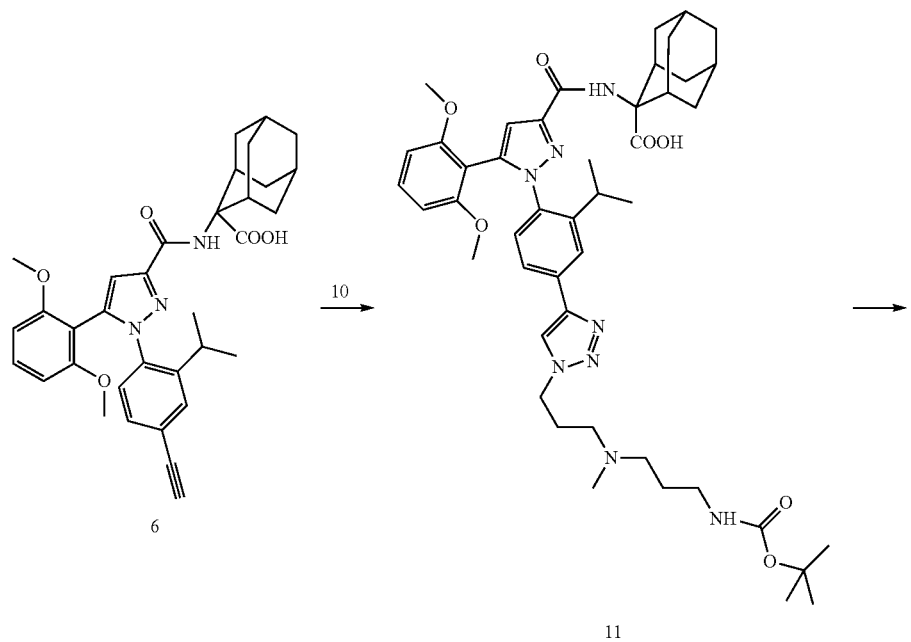
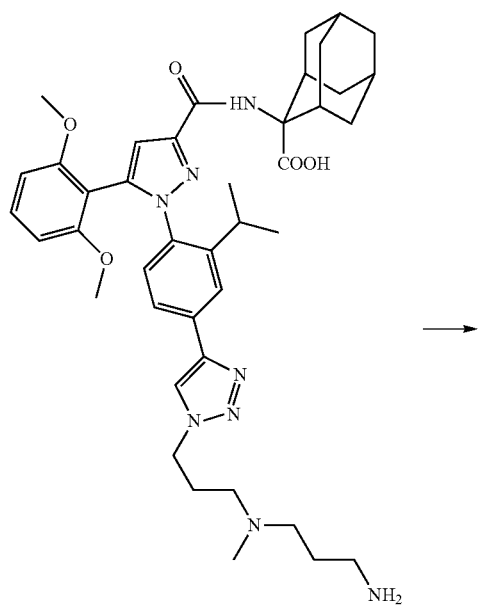

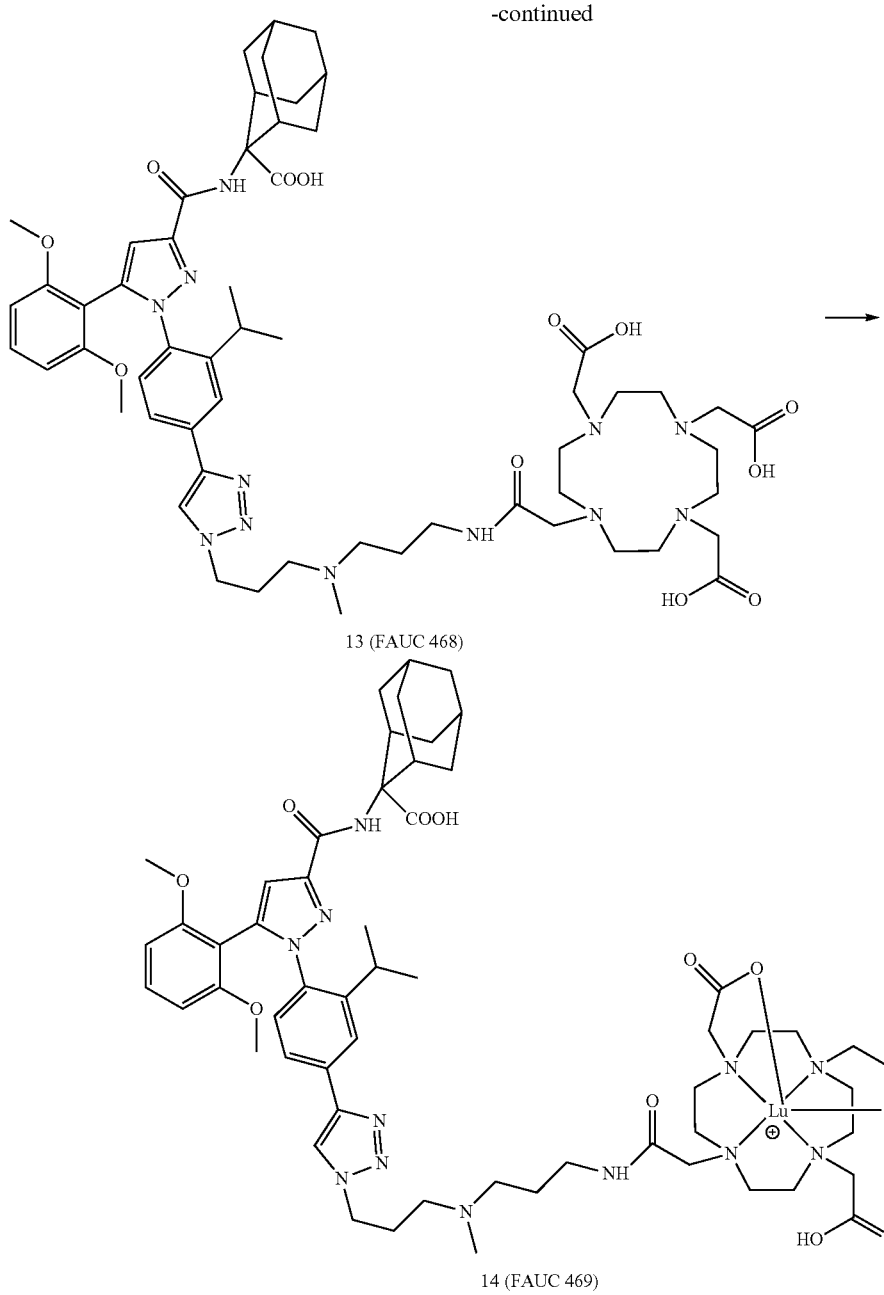

13 (FAUC 468)

14 (FAUC 469)

Methyl 4-(2,6-dimethoxyphenyl)-2,4-dioxobutyrate (1)

To a solution of 7 g (38.8 mmol) 2,6-dimethoxyacetophenon in 120 ml dry methanol aws added 31.6 ml (232 mmol) diethyloxalate. The mixture was cooled to 0° C., treated with 1.78 g (77.6 mmol) sodium and stirred for 18 h at 40° C. The pH was adjusted to mildly acidic by the addition of 2N—HCl and the mixture was extracted with diethylether/H$_2$O. The combined organic layers were dried, evaporated and the residue was stored for 2 h in the fridge. The resulting solid was separated from the liquid by filtration and washing with cooled ethanol. The filtrate was concentrated and as described above treated to obtain another product fraction. The solid was dissolved in methanol and stirred overnight. Evaporation of the solvent yielded the desired compound as a yellow solid (7.9 g, 87%).

$^1$H-NMR (360 MHz, CDCl$_3$) δ (ppm): 3.82 (s, 6H), 3.90 (s, 3H), 6.58 (d, J=8.5 Hz, 2H), 6.62 (s, 1H), 7.34 (t, J=8.5 Hz, 1H), 14.3 (br s, 1H)

4-Bromo-2-isopropylaniline (2)

To a solution of 2-isopropylaniline (2.70 g, 2.83 mL, 20 mmol) and NH$_4$OAc (154 mg, 2 mmol) in acetonitrile (100 mL) was added N-bromosuccinimide (3.74 g, 21 mmol). The mixture was stirred at room temperature for 10 min followed by concentration in vacuo. After addition of H$_2$O and extraction with ethyl acetate, the organic layer was dried (MgSO$_4$), evaporated and the residue was purified by flash column chromatography (cyclohexane/ethyl acetate 10:1) to give 2 (3.45 g, 81%) as a brown oil.

$^1$H NMR (360 MHz, CDCl$_3$): δ=1.17 (d, J=6.8 Hz, 6H), 2.77 (hept, J=6.8 Hz, 1H), 3.56 (br s, 2H), 6.48 (d, J=8.4 Hz, 1H), 7.03 (dd, J=8.4, 2.3 Hz, 1H), 7.14 (d, J=2.3 Hz, 1H).

MS (APCI): m/z 213.9 [M+H]$^+$ and 215.9 [M+H]$^+$.

Methyl 1-(4-bromo-2-isopropylphenyl)-5-(2,6-dimethoxyphenyl)-1H-pyrazole-3-carboxylate (3)

Concentrated aqueous hydrochloric acid (32 mL) was added to vigorously stirred 2 (4 g, 18.7 mmol) at 0° C. After 15 min a solution of NaNO$_2$ (1.27 g, 18.4 mmol) in H$_2$O (7.8 mL) was added over a period of 15 min. This mixture was additionally stirred for 15 min followed by addition of SnCl$_2$ dihydrate (9.37 g, 41 mmol) in concentrated HCl (9.4 mL) and 30 min of stirring without cooling. 1 (4.97 g, 18.7 mmol) in ethanol (160 mL) was added to the reaction mixture and refluxed for 20 min. After neutralization with 50% aqueous NaOH solution, the mixture was concentrated in vacuo, treated with H$_2$O and extracted with ethyl acetate. The combined organic layers were dried (MgSO$_4$), evaporated and the residue was purified by flash column chromatography (cyclohexane/ethyl acetate 25:2) to give 3 (4.80 g, 56%) as colorless solid.

Mp 181° C.

IR: (NaCl): 2965, 1723, 1605, 1589, 1475, 1253, 1230, 1111 cm$^{-1}$.

$^1$H NMR (360 MHz, CDCl$_3$): δ=0.95 (br s, 6H), 2.65 (hept, J=6.9 Hz, 1H), 3.64 (s, 6H), 3.94 (s, 3H), 6.46 (d, J=8.4 Hz, 2H), 6.93 (s, 1H), 7.20 (d, J=8.4 Hz, 1H), 7.25 (dd, J=8.4, 2.2 Hz, 1H), 7.25 (t, J=8.4 Hz, 1H), 7.31 (d, J=2.2 Hz, 1H).

$^{13}$C NMR (90 MHz, CDCl$_3$): δ=23.8, 27.7, 51.9, 55.5, 103.5, 106.7, 111.2, 123.2, 128.4, 129.1, 130.0, 131.4, 137.0, 138.9, 143.6, 148.2, 158.3, 163.1.

MS (APCI): m/z 459.1 [M+H]$^+$ and 461.0 [M+H]$^+$.

Methyl 5-(2,6-dimethoxyphenyl)-1-(2-isopropyl-4-((trimethylsilyl)ethynyl)phenyl)-1H-pyrazole-3-carboxylate (4)

A mixture of compound 3 (1 g, 2.2 mmol), trimethylsilylacetylene (0.9 mL, 6.5 mmol), bistriphenylphosphinepalladium-(II)-dichloride, CuI (41 mg, 0.21 mmol), triethylamine (0.9 mL, 6.5 mmol) in 5 mL toluene was heated in a sealed tube at 120° C. for 2 hrs. It was then cooled down to room temperature and the solvent was evaporated in vacuo. The product was then purified by flash chromatography with 7:3 (hexane:ethylacetate) to yield compound 4 (0.566 g) in 55% yield.

$^1$H-NMR (300 MHz, CDCl$_3$): δ (ppm) 0.24 (s, 9H), 0.95 (d, J=6.9 Hz, 6H), 2.66 (hept, J=6.9 Hz, 1H), 3.63 (s, 6H), 3.94 (s, 3H), 6.43 (d, J=8.4 Hz, 2H), 6.94 (s, 1H), 7.19 (d, J=8.5 Hz, 1H), 7.22 (t, J=8.4 Hz, 1H), 7.20-7.25 (m, 1H), 7.29-7.31 (m, 1H).

$^{13}$C-NMR (150 MHz, CDCl$_3$): δ (ppm) −1.9, 27.0, 27.5, 52.0, 55.5, 95.0, 103.6, 104.8, 106.9, 111.4, 123.9, 128.5, 128.9, 129.9, 131.4, 138.1, 139.0, 143.6, 146.0, 158.4, 163.3.

LC-MS-APCI: m/z Calcd. for C$_{27}$H$_{32}$N$_2$O$_4$Si: 477.2, [M+H]$^+$: m/z Found: 477.2 [M+H]$^+$

5-(2,6-Dimethoxyphenyl)-1-(4-ethynyl-2-isopropylphenyl)-1H-pyrazole-3-carboxylic Acid (5)

Compound 4 (0.46 g, 0.96 mmol) was dissolved in 3 mL methanol and K$_2$CO$_3$ (0.5 g, 0.5 mmol) was added and the reaction mixture was stirred at room temperature for 1 hour. The solvent was evaporated and the product was separated and purified by flash chromatography (ethylacetate with 0.1% HCOOH) to give 0.23 g (61%) of compound 5.

$^1$H-NMR (360 MHz, CDCl$_3$): δ (ppm) 0.98 (d, J=7.0 Hz, 6H), 2.69 (hept., J=7.0 Hz, 1H), 3.09 (s, 1H), 3.64 (s, 6H), 6.45 (d, J=8.4 Hz, 2H), 6.98 (s, 1H), 7.24 (t, J=8.4 Hz, 1H), 7.25-7.26 (m, 2H), 7.35-7.37 (m, 1H).

$^{13}$C-NMR (90 MHz, CDCl$_3$): δ (ppm) 23.7, 27.5, 56.0, 82.3, 83.3, 104.3, 106.4, 111.3, 123.3, 128.6, 129.4, 130.0, 132.2, 138.2, 139.1, 144.5, 146.4, 158.5, 163.8.

LC-MS-APCI: m/z Calcd. for C$_{23}$H$_{22}$N$_2$O$_4$: 391.2, [M+H]$^+$: m/z Found: 391.1 [M+H]$^+$, purity by HPLC (Agilent 1100 analytical series, column: Zorbax Eclipse XDB-C8 analytical column, 4.6×150 mm, 5 μm, flow rate: 0.5 ml/min, detection wavelength: 254 nm, acetonitrile/H$_2$O 0.1% TFA as the solvent system and employing the following gradient system in 0-21 min: 10-100% acetonitrile, 21-24 min: 100% acetonitrile, 24-27 min 100-10% acetonitrile): 99%, t$_R$=12.5 min.

2-(5-(2,6-Dimethoxyphenyl)-1-(4-ethynyl-2-isopropylphenyl)-1H-pyrazole-3-carboxamido) adamantane-2-carboxylic Acid (6)

Compound 5 (229 mg, 0.59 mmol) was dissolved in 5 mL acetonitrile in a Schlenk flask under nitrogen atmosphere and trimethylamine (0.160 mL, 1.2 mmol) and isobutylchloroformate (92 μL, 0.70 mmol) were added and the reaction was stirred at room temperature for 30 minutes to obtain a first reaction mixture. 2-Aminoadamantane-2-carboxylic acid hydrochloride (172 mg, 0.89 mmol) was suspended in 5 mL of acetonitrile in a microwave vial and to this trimethylamine (0.24 mL, 1.8 mmol) and trimethylsilyl chloride (0.21 mL, 1.8 mmol) were added and it was stirred for 5 min at room temperature. Thereafter, the first reaction mixture was added to this microwave vial and heated at 80° C. in a sealed tube for 16 hrs. Then it was cooled and acidified with 2N HCl, and extracted with dichloromethane, the organic phase dried with Na$_2$SO$_4$ and purified by preparative HPLC. Column ZORBAX ECLIPSE XDB-C8 (21.2×150 mm), 5 μm, flow rate 12 mL/min. Solvent methanol, water 0.1% HCOOH, gradient 40-95% methanol in 20 min, 95-95% in 24 min, 95-40% in 27 min, product peak appeared at 23 min. Yield 250 mg, 75%.

$^1$H-NMR (360 MHz, CDCl$_3$): δ (ppm) 1.04 (d, J=7.0 Hz, 6H), 1.59-1.84 (m, 8H), 1.93-2.01 (m, 2H), 2.05-2.15 (m, 2H), 2.51-2.56 (m, 2H), 2.62 (hept., J=7.0 Hz, 1H), 3.64 (s, 6H), 4.24 (s, 1H), 6.61 (d, J=8.4 Hz), 6.69 (s, 1H), 7.14 (d, J=8.5 Hz, 1H), 7.26 (dd, J=8.5 Hz, 1.9 Hz, 1H), 7.30 (t, J=8.4 Hz, 1H), 7.35 (bs, 1H), 7.45 (d, J=1.9 Hz, 1H).

$^{13}$C-NMR (90 MHz, CDCl$_3$); δ (ppm) 23.3, 26.0, 26.3, 27.2, 31.9, 32.5, 33.3, 37.2, 55.6, 62.2, 81.7, 82.7, 103.7, 106.0, 108.2, 122.7, 127.4, 128.9, 129.7, 131.6, 137.3, 138.9, 146.0, 146.3, 157.9, 160.0, 173.1.

Calcd. for C$_{34}$H$_{37}$N$_3$O$_5$: 568.2, [M+H]$^+$: m/z Found: 568.1 [M+H]$^+$, purity by HPLC (Agilent 1100 analytical series, column: Zorbax Eclipse XDB-C8 analytical column, 4.6×150 mm, 5 μm, flow rate: 0.5 ml/min, detection wavelength: 254 nm, methanol/H$_2$O 0.1% HCOOH as the solvent system and employing the following gradient system in 0-21 min: 10-100% methanol, in 21-24 min: 100% methanol, 24-27 min: 100-10% methanol, flow rate: 0.5 ml/min): 97%, t$_R$=16.0 min.

Tert-butyl (3-hydroxypropyl)carbamate (7)

3-Aminopropanol (100 mg, 1.3 mmol) was dissolved in 5 mL tetrahydrofuran. 2 mL 2N NaOH solution followed by Boc-anhydride (435 mg, 2 mmol) were added and the reaction mixture was stirred at room temperature for 16 hours. The product was then extracted with ethylacetate and the organic layer was dried with $Na_2SO_4$. The product was purified by flash chromatography using hexane:ethylacetate (6:3) to yield 230 mg (98%) of the product as a colorless oil.

$^1$H-NMR (600 MHz, $CDCl_3$): δ (ppm) 1.45 (s, 9H), 1.64-1.68 (m, 2H), 2.94 (s, 1H), 3.29 (q, J=6.2 Hz, 2H), 3.66 (q, J=5.7 Hz, 2H), 4.77 (s, 1H).

Tert-butyl (3-oxopropyl)carbamate (8)

Compound 7 (58 mg, 0.32 mmol) was dissolved in 1 mL DMSO and 1 mL dichloromethane and cooled to 0° C. $NEt_3$ (0.07 mL, 0.5 mmol) and pyridine sulfurtrioxide complex (79 mg, 0.5 mmol) were added. The reaction mixture was then warmed up to room temperature and stirred for 1 h. 3 mL water were then added and the organic layer was extracted three times with dichloromethane and dried with $Na_2SO_4$ and concentrated in vacuo. The crude product was used for the next step.

Tert-butyl (3-((3-chloropropyl)(methyl)amino)propyl)carbamate (9)

The aldehyde 8 (57 mg, 0.329 mmol) was dissolved in 3 mL dichloromethane and cooled to 0° C. To this mixture chloro-N-methylpropylamine hydrochloride (53 mg, 0.49 mmol) was added followed by $Na(OAc)_3BH$ (104 mg, 0.49 mmol) and the reaction mixture was stirred at 0° C. for 1 h. It was then warmed up to room temperature and stirred at room temperature for 16 h. The reaction was quenched with a saturated aqueous solution of $NaHCO_3$ and extracted three times with dichloromethane. The combined organic phases were dried over anhydrous $Na_2SO_4$ and concentrated in vacuo to obtain the crude product. The product was purified by flash chromatography (20% methanol in ethyl acetate and 0.1% $NH_3$) to give 54 mg (62%) of 10 as a colorless oil.

$^1$H-NMR (600 MHz, $CDCl_3$): δ (ppm) 1.44 (s, 9H), 1.66 (quint, J=6.5 Hz, 2H), 1.94 (quint, J=6.6 Hz, 2H), 2.23 (s, 3H), 2.45 (t, J=6.5 Hz, 2H), 2.51 (t, J=6.5 Hz, 2H), 3.19 (q, J=6 Hz, 2H), 3.60 (t, J=6.6 Hz, 2H).

Tert-butyl (3-((3-azidopropyl)(methyl)amino)propyl) carbamate (10)

Compound 9 (17 mg, 64 μmol) was dissolved in 5 mL acetonitrile and 1 mL water mixture and to this KI (32 mg, 0.2 mmol) and $NaN_3$ (12 mg, 0.2 mmol) were added and the reaction mixture was refluxed for 16 h. The reaction was quenched with a saturated aqueous solution of $NaHCO_3$ and extracted three times with ethyl acetate. The combined organic phases were dried over anhydrous $Na_2SO_4$ and concentrated in vacuo to obtain the crude product which was used for the next step without further purification.

2-(1-(4-(1-(3-((Tert-butoxycarbonyl)amino)propyl)(methyl)amino)propyl)-1H-1,2,3-triazol-4-yl)-2-isopropylphenyl)-5-(2,6-dimethoxyphenyl)-1H-pyrazole-3-carboxamido)adamantane-2-carboxylic Acid (11)

To the mixture of 6 (15 mg, 26 μmol) and 10 (11 mg, 40 μmol) in a solvent system of methanol-$H_2O$—$CH_2Cl_2$ (1:1:1) were added $CuSO_4.5H_2O$ (6 mg, 26 μmol) and sodium ascorbate (5 mg, 26 μmol) and the mixture was stirred overnight at room temperature. After the completion of the reaction (monitored by TLC), the reaction mixture was quenched by the addition of 0.1 M EDTA aqueous solution. The organic compounds were extracted with $CH_2Cl_2$ (3 times), the organic phase dried over $Na_2SO_4$ and evaporated. The pure compound was isolated by HPLC. Column Nucleodur C18 HTec, 32×250 mm, 5 μm particles, flow rate 32 mL/min, solvent acetonitrile, $H_2O$ (0.1% TFA), 10-100% acetonitrile in 0-18 min. 80-100% acetonitrile in 20 min. 100-100% acetonitrile in 23 min, 100-10% acetonitrile in 24 min, 10-10% acetonitrile in 27 min. The product peak was observed at 15 min. Yield 14 mg (60%).

$^1$H-NMR (600 MHz, $CD_3OD$): δ (ppm) 1.13 (d, J=6.4 Hz, 6H), 1.40 (s, 9H), 1.76-1.90 (m, 10H), 2.14 (d, J=13.3 Hz, 2H), 2.24 (d, J=13.3 Hz, 2H), 2.43 (bs, 2H), 2.65 (s, 2H), 2.79 (hept, J=6.8 Hz, 1H), 2.89 (s, 3H), 3.12-3.29 (m, 6H), 3.69 (s, 6H), 4.60 (t, J=6.4 Hz, 2H), 6.58 (d, J=8.5 Hz, 2H), 6.79 (s, 1H), 7.28 (t, J=8.7 Hz, 1H), 7.36 (d, J=8.7 Hz, 1H), 7.58 (s, 1H), 7.62 (dd, J=8.1, 1.9 Hz, 1H), 7.83 (d, J=1.9 Hz, 1H), 8.41 (s, 1H).

Calcd. for $C_{46}H_{62}N_8O_7$— Boc group: 739.6, $[M+H-Boc]^+$: m/z Found: 739.6 $[M+H-Boc]^+$, purity by HPLC (Agilent 1100 analytical series, column: Zorbax Eclipse XDB-C8 analytical column, 4.6×150 mm, 5 μm, flow rate: 0.5 ml/min, detection wavelength: 254 nm, methanol/$H_2O$ 0.1% HCOOH as the solvent system and employing the following gradient system in 0-12 min: 10-100% methanol, in 12-15 min: 100% methanol, 15-18 min: 100-10% methanol, flow rate: 0.5 ml/min): 97%, $t_R$=11.8 min.

2-(1-(4-(1-(3-((3-Aminopropyl)(methyl)amino)propyl)-1H-1,2,3-triazol-4-yl)-2-isopropylphenyl)-5-(2,6-dimethoxyphenyl)-1H-pyrazole-3-carboxamido)adamantane-2-carboxylic Acid (12)

Compound 11 (11 mg, 13 μmol) was dissolved in 2 mL ethyl acetate, a solution of 2M HCl in diethylether (0.5 mL, 1 mmol) was added and the reaction mixture was stirred at room temperature for 16 h. The organic compounds were extracted with ethyl acetate (3 times), dried over $Na_2SO_4$ and evaporated. The pure compound was isolated by HPLC using column Nucleodur C18 HTec, 32×250 mm, 5 μm particles, flow rate 32 mL/min, solvent methanol, $H_2O$ (0.1% HCOOH), 0-10% methanol in 0-2 minutes, 10-100% methanol in 0-12 minutes, 100-100% methanol in 12-15 minutes, 100-10% methanol in 15-16 minutes, 10-10% in 16-18 minutes. Product peak appeared at 11 minutes. Yield 9 mg (92%).

$^1$H-NMR (600 MHz, $CD_3OD$): δ (ppm) 1.13 (d, J=6.4 Hz, 6H), 1.74-1.85 (m, 8H), 2.09-2.14 (m, 4H), 2.24 (d, J=13.3 Hz, 2H), 2.45 (quint, J=7.3 Hz, 2H), 2.64 (bs, 2H), 2.79 (hept, J=6.8 Hz, 1H), 2.89 (s, 3H), 3.03 (t, J=7.6 Hz, 2H), 3.24-3.27 (m, 3H), 3.69 (s, 6H), 4.60 (t, J=6.4 Hz, 2H), 6.57 (d, J=8.5 Hz, 2H), 6.79 (s, 1H), 7.28 (t, J=8.7 Hz, 1H), 7.34 (d, J=8.7 Hz, 1H), 7.62 (dd, J=8.1, 1.9 Hz, 1H), 7.83 (d, J=1.9 Hz, 1H), 8.41 (s, 1H).

$^{13}$C-NMR (150 MHz, $CD_3OD$); δ (ppm) 23.6, 25.8, 28.0, 28.2, 28.5, 29.0, 34.0, 34.1, 35.0, 37.9, 38.9, 40.7, 48.4, 54.4, 54.8, 56.2, 64.7, 104.7, 107.9, 109.9, 123.3, 123.9, 124.4, 129.7, 132.8, 132.9, 138.8, 147.3, 148.2, 148.4, 159.9, 162.9, 163.1, 163.4, 175.7.

LC-MS-ESI: m/z Calcd. for $C_{41}H_{54}N_8O_5$: 739.4, $[M+H]^+$: m/z Found: 739.6 $[M+H]^+$, purity by HPLC (Agilent 1100 analytical series, column: Zorbax Eclipse XDB-C8 analytical column, 4.6×150 mm, 5 μm, flow rate: 0.5 ml/min, detection wavelength: 254 nm, methanol/$H_2O$ 0.1% HCOOH as the solvent system and employing the following gradient system in 0-12 min:

10-100% methanol, in 12-15 min: 100% methanol, 15-18 min: 100-10% methanol, flow rate: 0.5 ml/min): 99%, $t_R$=10.6 min.

Fauc 468 (13)

Compound 12 (9 mg, 12 μmol) was dissolved in 2 mL dimethylformamide and trimethylamine (3 μL, 18 μmol) was added followed by DOTA-NHS ester (9 mg, 18 μmol) and the reaction mixture was stirred at room temperature for 16 h. The solvent was evaporated to dryness and the product was purified by HPLC Column ZORBAX Eclipse XDB C8 HTec, 21.2×250 mm, 5 μm particles, flow rate 12 mL/min, solvent methanol, H$_2$O (0.1% HCOOH), 10-80% methanol in 0-18 min. 80-100% methanol in 20 min. 100-10% methanol in 22 min, 10-10% methanol in 25 min. The product peak was observed at 20 min. Yield 11.5 mg (84%).

MS-ESI: m/z calcd. for $C_{57}H_{80}N_{12}O_{12}$: 563.5, [M+2H]$^{2+}$: m/z found: 563.8 [M+2H]$^{2+}$, purity by HPLC (Agilent 1100 analytical series, column: Zorbax Eclipse XDB-C8 analytical column, 4.6×150 mm, 5 μm, flow rate: 0.5 ml/min, detection wavelength: 254 nm, methanol/H$_2$O 0.1% HCOOH as the solvent system and employing the following gradient system in 0-12 min: 10-100% methanol, in 12-15 min: 100% methanol, 15-18 min: 100-10% methanol, flow rate: 0.5 ml/min): 95%, $t_R$ 12.0 min.

HRMS: $C_{57}H_{81}N_{12}O_{12}$: 1125.61067, found 1125.60914.

Fauc 469 (14)

Compound 13 (6.5 mg, 6 μmol) was dissolved in 2 mL HEPES buffer and the pH was adjusted to 5 with 0.2 N HCl solution and Lu(NO$_3$)$_3$ (6.57 mg, 17 μmol) was added and the reaction mixture was stirred at 98° C. for 10 min. The product was purified by HPLC Column ZORBAX Eclipse XDB C8 HTec, 21.2×250 mm, 5 μm particles, flow rate 12 mL/min, solvent methanol/H$_2$O 0.1% HCOOH as the solvent system and employing the following gradient system in 0-12 min: 10-100% methanol, in 12-15 min: 100% methanol, 15-18 min: 100-10% methanol, flow rate: 12 ml/min. The product peak was observed at 11.7 min. Yield 6 mg (80%).

MS-ESI: m/z Calcd. for $C_{57}H_{78}LuN_{12}O_{12}$: 650.1, [M+2H]$^{2+}$: m/z Found: 649.6 [M+2H]$^{2+}$, purity by HPLC (Agilent 1100 analytical series, column: Zorbax Eclipse XDB-C8 analytical column, 4.6×150 mm, 5 μm, flow rate: 0.5 ml/min, detection wavelength: 254 nm, methanol/H$_2$O 0.1% HCOOH as the solvent system and employing the following gradient system in 0-12 min: 10-100% methanol, in 12-15 min: 100% methanol, 15-18 min: 100-10% methanol, flow rate: 0.5 ml/min): 98%, $t_R$=11.3 min.

HRMS: $C_{57}H_{78}LuN_{12}O_{12}$: 1297.52524, found: 1297.52644.

Example 2

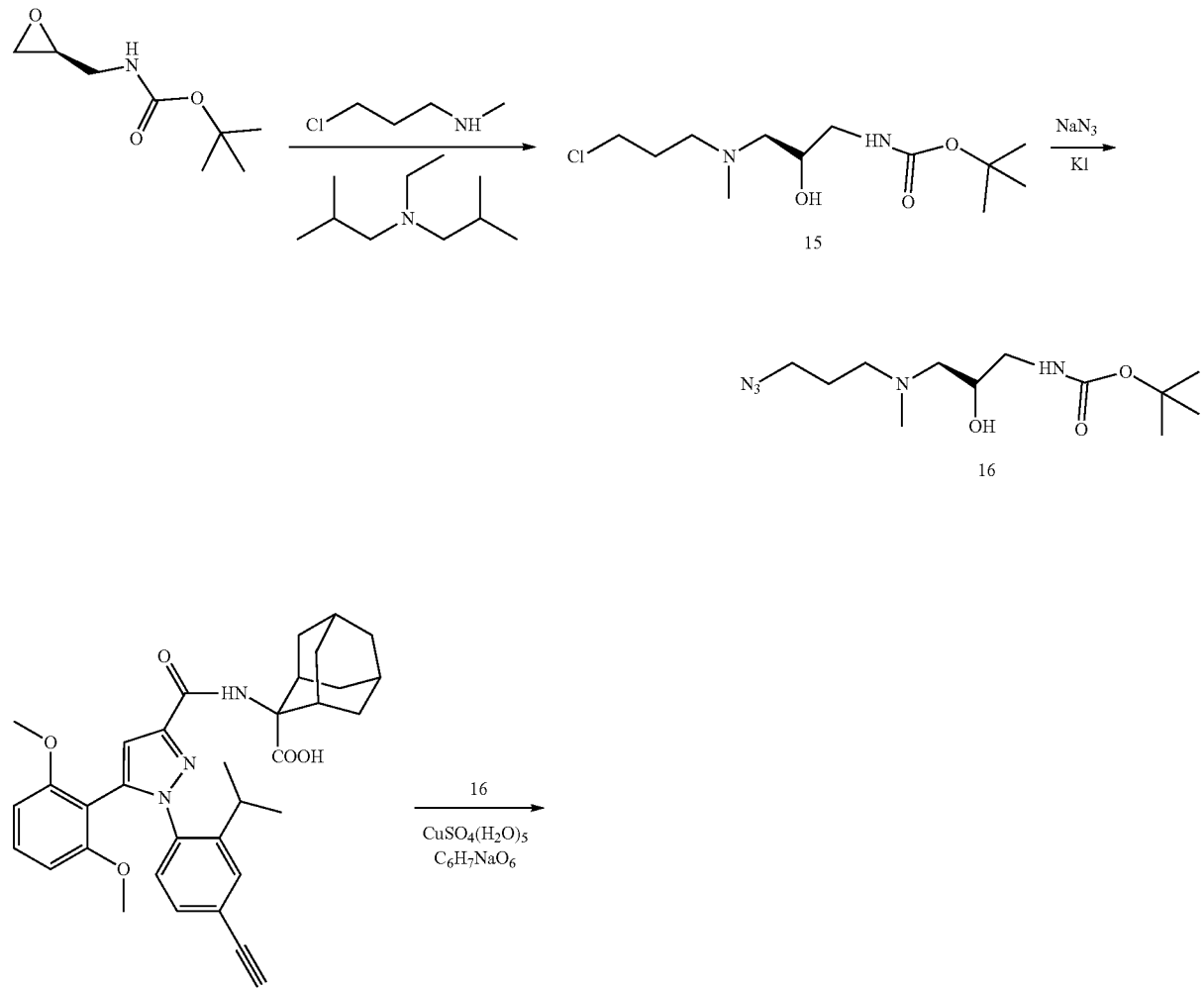

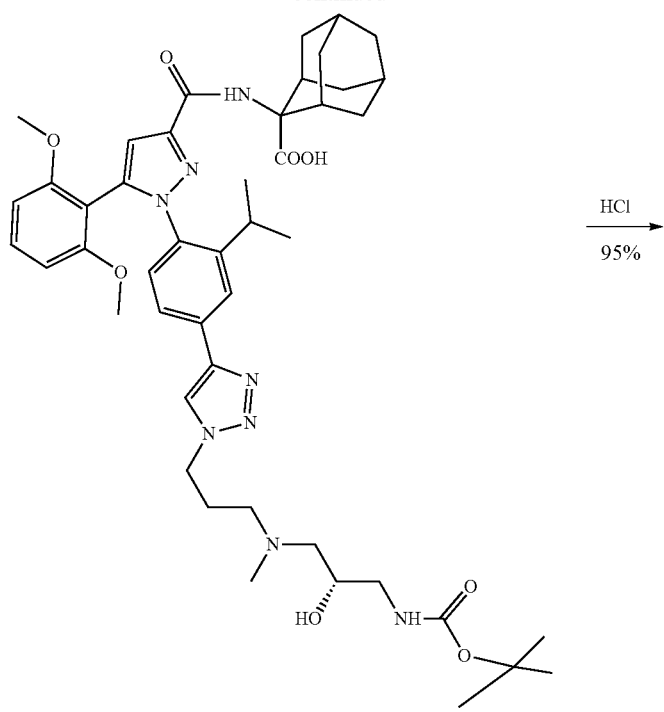
17
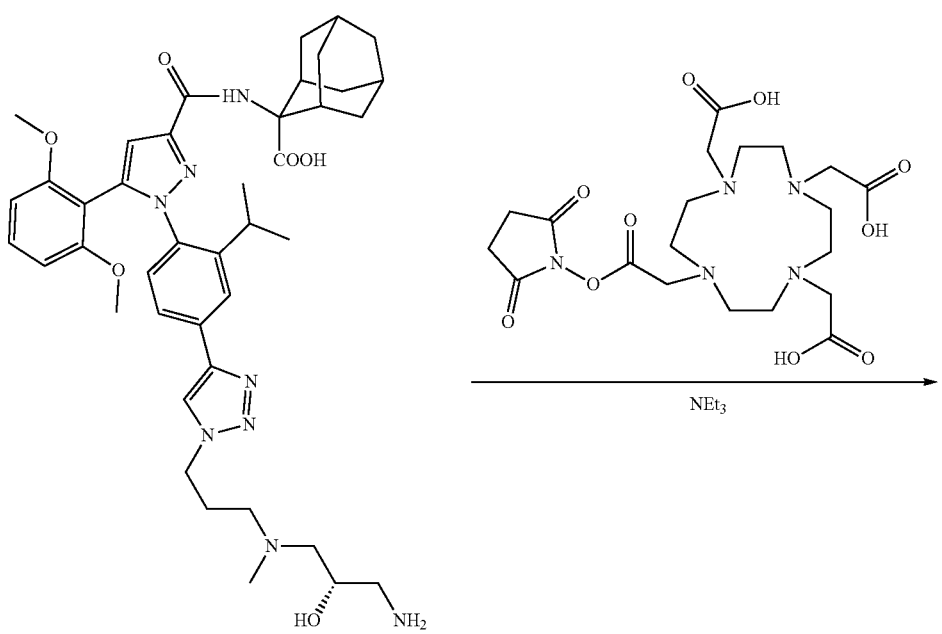
18

-continued

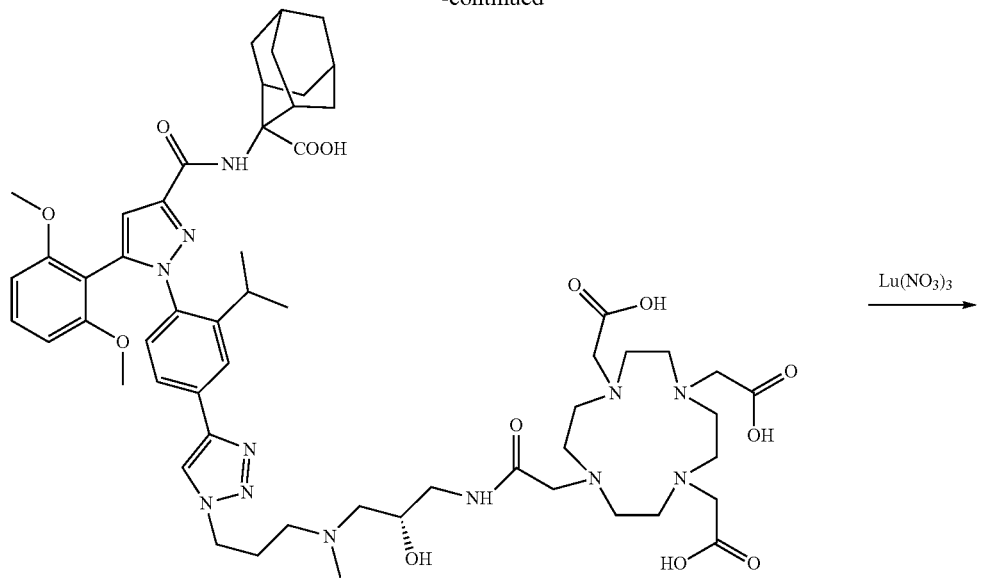

19 (FAUC 550)

Lu(NO₃)₃ →

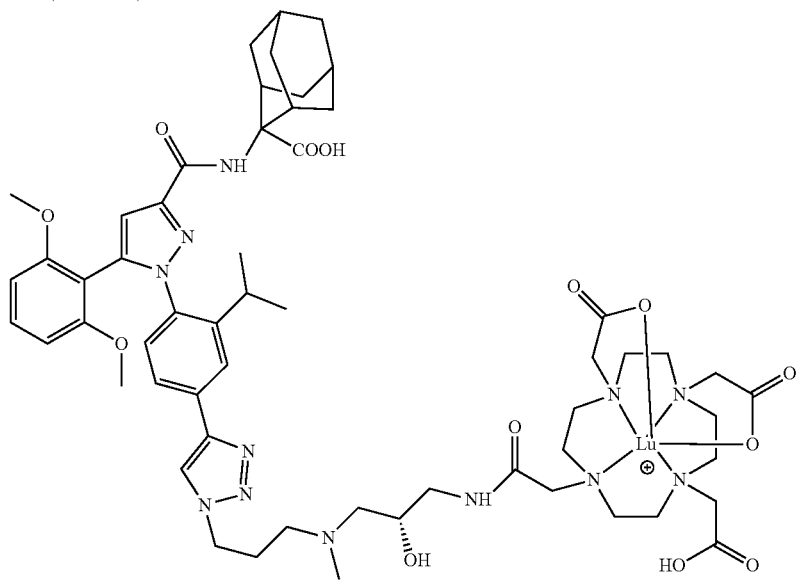

20 (FAUC 551)

Tert-butyl (S)-(3-((3-chloropropyl)(methyl)amino)-2-hydroxypropyl)carbamate (15)

(S)—N-Boc-2,3-epoxypropylamine (50 mg, 0.3 mmol) was dissolved in 5 mL acetonitrile. 3-Chloro-N-methylpropan-1-amine (46 mg, 0.43 mmol) and DIPEA (0.1 mL, 0.46 mmol) were added and the reaction mixture was stirred at room temperature for 16 hrs. The product was then extracted with ethyl acetate and the organic layer was dried with Na₂SO₄. The product was purified by flash chromatography using hexane:ethylacetate (7:3) to yield 43 mg (53%) of the product as a colorless oil.

¹H-NMR (600 MHz, CDCl₃): δ (ppm) 1.45 (s, 9H), 1.93 (p, J=6.4 Hz, 2H), 2.26 (s, 3H), 2.30-2.38 (m, 2H), 2.48-2.52 (m, 1H), 2.64-2.68 (m, 1H), 3.01-3.06 (m, 1H), 3.32-3.36 (m, 1H), 3.58 (t, J=6.4 Hz, 2H), 3.73-3.76 (m, 1H), 4.97 (bs, 1H).

LC-MS-ESI: m/z Calcd. for $C_{12}H_{25}ClN_2O_3$: 281.1, [M+H]⁺: m/z Found: 281.0 [M+H]⁺

Tert-butyl (S)-(3-((3-azidopropyl)(methyl)amino)-2-hydroxypropyl)carbamate (16)

Compound 15 (35 mg, 0.124 mmol) was dissolved in a mixture of 5 mL acetonitrile and 1 mL water and to this KI (62 mg, 0.4 mmol) and NaN₃ (24 mg, 0.4 mmol) were added and the reaction mixture was refluxed for 16 h. The reaction was quenched with a saturated solution of NaHCO₃ and extracted three times with ethyl acetate. The combined organic phases were dried over anhydrous Na$_2$SO$_4$ and concentrated in vacuo to obtain the crude product which was used for the next step without further purification.

(1R,3S,5R,7R)-2-(1-(4-(1-(3-((3-((Tert-butoxycarbonyl)amino)-2-hydroxypropyl) (methyl)amino)propyl)-1H-1,2,3-triazol-4-yl)-2-isopropylphenyl)-5-(2,6-dimethoxyphenyl)-1H-pyrazole-3-carboxamido) adamantane-2-carboxylic Acid (17)

To the mixture of 6 (50 mg, 88 μmol) and 16 (35 mg, 122 μmol) in a solvent system of methanol-H$_2$O—CH$_2$Cl$_2$ (1:1:1) was added CuSO$_4$.5H$_2$O (2 mg, 8.8 μmol) and sodium ascorbate (3.5 mg, 17 μmol) and the reaction mixture was stirred overnight at room temperature. After the completion of the reaction (monitored by TLC), the reaction mixture was quenched by the addition of 0.1 M EDTA aqueous solution. The organic compounds were extracted with CH$_2$Cl$_2$ (3 times), the organic phase was dried over Na$_2$SO$_4$ and evaporated. The pure compound was isolated by HPLC using column Nucleodur C8 HTec, 21.2×250 mm, 5 μm particles, flow rate 12 mL/min, solvent acetonitrile, H$_2$O (0.1% HCOOH), 10-100% acetonitrile in 0-10 min., 100-100% acetonitrile in 10-12 minutes, 100-10% acetonitrile in 12-13 minutes, 10-10% acetonitrile in 13-15 minutes. The product peak was observed at 8 min. Yield was 45 mg (60%).

$^1$H-NMR (600 MHz, CDCl$_3$): δ (ppm) 1.14 (d, J=6.4 Hz, 6H), 1.42 (s, 9H), 1.70-1.88 (m, 8H), 2.07 (d, J=13.3 Hz, 2H), 2.23-2.28 (m, 4H), 2.50 (s, 3H), 2.57 (d, J=13.1 Hz, 1H), 2.67-2.81 (m, 6H), 3.05-3.09 (m 1H), 3.32-3.35 (m, 1H), 3.61 (s, 6H), 3.92-3.94 (m, 2H), 4.47 (t, J=6.7 Hz, 2H), 5.16 (s, 1H), 6.43 (d, J=8.5 Hz, 2H), 6.86 (s, 1H), 7.11 (d, J=8.1 Hz, 1H), 7.21 (t, J=8.7 Hz, 1H), 7.33 (s, 1H), 7.38 (dd, J=8.1, 1.9 Hz, 1H), 7.83 (d, J=1.9 Hz, 1H), 7.85 (s, 1H).

$^{13}$C-NMR (150 MHz, CDCl$_3$): δ (ppm) 24.9, 25.6, 26.7, 26.9, 27.9, 28.4, 32.5, 32.8, 33.8, 33.9, 37.7, 41.8, 44.3, 47.6, 54.4, 55.5, 60.9, 64.9, 66.4, 79.5, 103.4, 106.9, 109.0, 120.4, 122.9, 123.6, 127.6, 131.3, 137.1, 139.7, 145.5, 146.5, 147.2, 156.5, 158.4, 163.6, 174.0.

[α]$_{589}$=+6.6° (24° C., c=1.13, methanol).

HRMS: Calcd. for C$_{45}$H$_{62}$N$_8$O$_8$: 855.0, [M+H-Boc]$^+$: m/z Found: 855.4 [M+H-Boc]$^+$, purity by HPLC (system E): 97%, $t_R$=11.8 min

(1R,3S,5R,7R)-2-(1-(4-(1-(3-(((S)-3-Amino-2-hydroxypropyl)(methyl)amino)propyl)-1H-1,2,3-triazol-4-yl)-2-isopropylphenyl)-5-(2,6-dimethoxyphenyl)-1H-pyrazole-3-carboxamido)adamantane-2-carboxylic Acid (18)

Compound 17 (38 mg, 44 μmol) was dissolved in 2 mL ethyl acetate and a solution of 2M HCl in diethylether (0.5 mL, 1 mmol) was added and the reaction mixture was stirred at room temperature for 16 h. The solvent was evaporated in vacuum and the residue was dissolved in methanol and purified by HPLC (Column Nucleodur C8 HTec, 32×250 mm, 5 μm particles, flow rate 32 mL/min, solvent acetonitrile, H$_2$O (0.1% TFA), 10-80% acetonitrile in 0-20 minutes, 80-100% acetonitrile in 20-21 minutes, 100-100% acetonitrile in 21-24 minutes, 100-10% in 24-25 minutes, 10-10% acetonitrile in 25-27 minutes) Product peak was observed at 12.6 minutes. Yield 30 mg (89%).

$^1$H-NMR (600 MHz, CD$_3$OD): δ (ppm) 1.12 (d, J=6.7 Hz, 6H), 1.74-1.85 (m, 8H), 2.13 (d, J=13.1 Hz, 2H), 2.23 (d, J=12.5 Hz, 2H), 2.39-2.58 (m, 2H), 2.64 (bs, 2H), 2.79 (hept, J=6.8 Hz, 1H), 2.92-2.94 (m, 1H), 2.95 (s, 3H), 3.13 (dd, J=13.2, 3.2 Hz, 1H), 3.26-3.28 (m, 2H), 3.31 (p, J=1.7 Hz, 1H), 3.68 (s, 6H), 4.27-4.31 (m, 1H), 4.60 (t, J=6.6 Hz, 2H), 6.57 (d, J=8.5 Hz, 2H), 6.79 (s, 1H), 7.28 (t, J=8.7 Hz, 1H), 7.34 (d, J=8.7 Hz, 1H), 7.62 (dd, J=8.1, 1.9 Hz, 1H), 7.83 (d, J=1.9 Hz, 1H), 8.41 (s, 1H).

$^{13}$C-NMR (150 MHz, CD$_3$OD); δ (ppm) 24.0, 26.6, 26.8, 27.4, 32.4, 32.5, 33.4, 37.4, 42.1, 46.7, 46.8, 48.2, 48.3, 54.6, 57.7, 62.0, 103.1, 108.3, 121.6, 122.3, 122.8, 128.0, 131.1, 131.3, 137.1, 146.6, 146.8, 158.3, 159.6, 161.3, 161.5, 161.7, 173.9.

[α]$_{589}$=+3.2° (24° C., c=1.6, methanol).

LC-MS-ESI: m/z Calcd. for C$_{41}$H$_{54}$N$_8$O$_6$: 754.9, [M+H]$^+$: m/z Found: 755.3 [M+H]$^+$, purity by HPLC system E: 99%, $t_R$=10.6 min.

Fauc 550 (19)

Compound 18 (15 mg, 20 μmol) was dissolved in 2 mL dimethylformamide and trimethylamine (5 μL, 30 μmol) was added followed by DOTA-NHS ester (15 mg, 30 μmol) and the reaction mixture was stirred at room temperature for 16 h. The reaction mixture was evaporated to dryness to remove the dimethylformamide, the residue was dissolved in methanol and the product was purified by HPLC (Column ZORBAX Eclipse XDB C8 HTec, 21.2×250 mm, 5 μm particles, flow rate 10 mL/min, solvent acetonitrile, H$_2$O (0.1% HCOOH), 10-100% acetonitrile in 10 minutes, 100-100% acetonitrile in 12 minutes, 100-10% acetonitrile in 13 minutes, 10-10% acetonitrile in 15 minutes). The product peak was observed at 7.5 minutes. Yield was 11.5 mg (48%).

MS-ESI: m/z Calcd. for C$_{57}$H$_{80}$N$_{12}$O$_{13}$: 570.5, [M+2H]$^{2+}$: m/z Found: 570.2 [M+2H]$^{2+}$, purity by HPLC system E: 95%, $t_R$=12.0 min.

HRMS: C$_{57}$H$_{81}$N$_{12}$O$_{12}$: 1125.61067 found 1125.60914.

Fauc 551 (20)

Compound 19 (5 mg, 4.1 μmol) was dissolved in 2 mL HEPES buffer and the pH was adjusted to 5 with 0.2 N HCl solution and Lu(NO$_3$)$_3$ (5 mg, 12 μmol) was added and the reaction mixture was stirred at 98° C. for 10 minutes. The product was purified by HPLC (Column ZORBAX Eclipse XDB C8 HTec, 21.2×250 mm, 5 μm particles, flow rate 10 mL/min, solvent acetonitrile, H$_2$O (0.1% TFA), 10-100% acetonitrile in 10 min, 100-100% acetonitrile in 12 minutes, 100-10% acetonitrile in 13 minutes, 10-10% acetonitrile in 15 minutes). The product peak was observed at 8.1 minutes. Yield was 3 mg (55%).

MS-ESI: m/z Calcd. for C$_{57}$H$_{78}$LuN$_{12}$O$_{13}$: 658.1, [M+2H]$^{2+}$: m/z Found: 657.4 [M+2H]$^{2+}$, purity by HPLC system E: 98%, $t_R$=11.3 min.

HRMS: C$_{57}$H$_{78}$LuN$_{12}$O$_{12}$: 1314.2888, found: 1314.2888.

Example 3

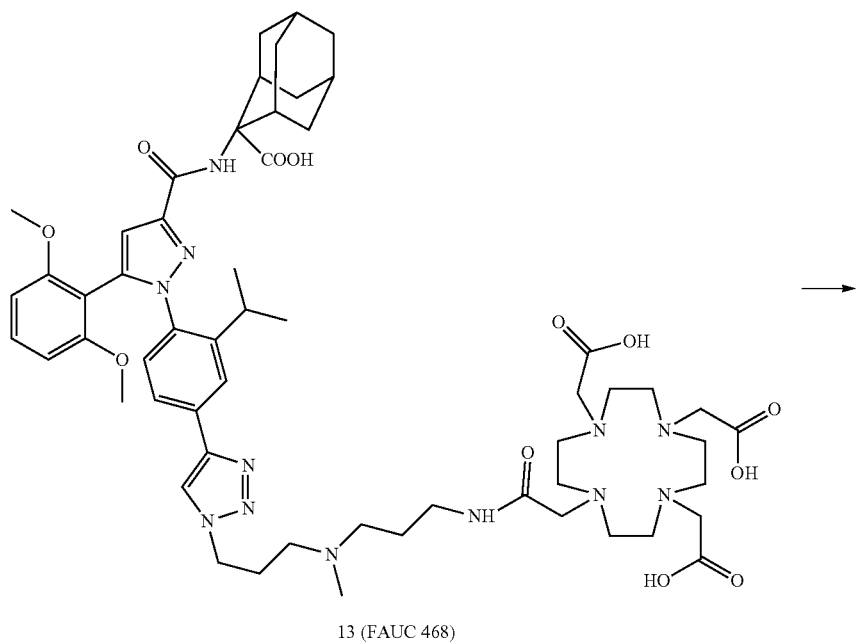

13 (FAUC 468)

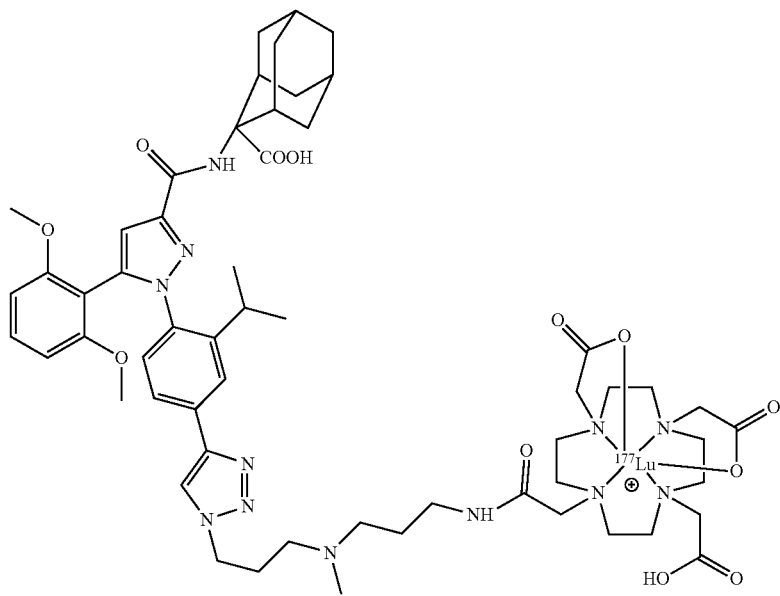

$^{177}$Lu-14 ((FAUC Lu469)

Radiosynthesis of $^{177}$Lu-14 (Fauc Lu469)

To a solution of 13 (2 nmol in 2 μL water) were added 200 μlL 0.5 M HEPES (4-(2-hydroxyethyl)-1-piperazineethanesulfonic acid) and 20 μL (200 MBq) n.c.a. $^{177}$LuCl$_3$ (in 0.04 M HCl). This mixture was allowed to react in a heat block at 98° C. After 10 min the radiochemical yield of $^{177}$Lu-14 was >99% as determined by radio-HPLC: Chromolith RP-18e, 10-100% acetonitrile in water (0.1% TFA) in a linear gradient over 5 min; $t_R$=2.35 min.

$K_i$ Values

Affinities for NTS1 and NTS2 as well as for dopaminergic and serotonergic receptors were determined in competitive radioligand binding assays using appropriate radioligands as shown in Table 1. The results are displayed in the following table. The affinities for human NTS1 were high (0.19 nM and 1.4 nM) with high selectivity over dopamine D2 receptors.

TABLE 1

$K_i$ values of FAUC 468, FAUC 469, FAUC 550 and FAUC 551

| | $K_i$ values [nM] | | | | | |
|---|---|---|---|---|---|---|
| | 13 (FAUC 468) | 14 (FAUC 469) | 19 (FAUC 550) | 20 (FAUC 551) | Reference compound 1 | Reference compound 2 |
| hNTS1 ([³H]NT; CHO) | 1.9 | 0.19 | 1.6 | 1.4 | 0.46 | 0.18 |
| hNTS2 ([³H]NT (8-13); HEK) | 100 | 13 | 59 | 27 | 25 | 7.7 |
| hD1 ([³H] SCH 23990) | n.d. | >50000 | n.d. | n.d. | n.d. | >50000 |
| hD5 ([³H] SCH 23990) | n.d. | >50000 | n.d. | n.d. | n.d. | n.d. |
| hD2$_{long}$ ([³H] spiperone) | n.d. | >50000 | n.d. | n.d. | n.d. | 2600 |
| hD2$_{short}$ ([³H] spiperone) | n.d. | >50000 | n.d. | n.d. | n.d. | 1700 |
| hD3 ([³H] spiperone) | n.d. | >50000 | n.d. | n.d. | n.d. | >50000 |
| hD4.4 ([³H] spiperone) | n.d. | >50000 | n.d. | n.d. | n.d. | >50000 |
| p5-HT$_{1A}$ ([³H] WAY600135) | n.d. | >50000 | n.d. | n.d. | n.d. | n.d. |
| h5-HT$_2$ ([³H] ketanserin) | n.d. | >50000 | n.d. | n.d. | n.d. | n.d. |
| pα1 ([³H] prazosine) | n.d. | >50000 | n.d. | n.d. | n.d. | n.d. |

Reference compounds 1 and 2 have the following structure:

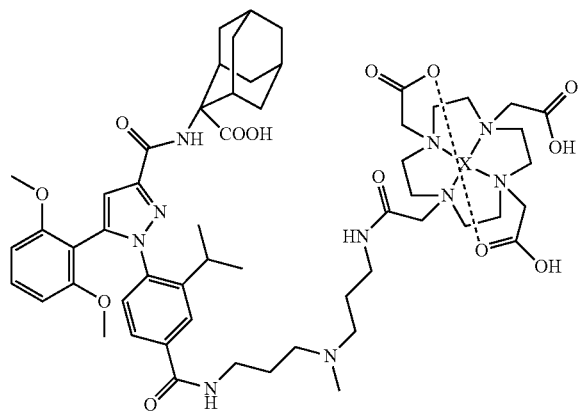

wherein in reference compound 1: X=Ga
and in reference compound 2: X=Lu.

Stability in Human Plasma

An aliquot of $^{177}$Lu-14 (FAUC Lu469) in PBS (50 µL) was added to human plasma (200 µL) and incubated at 37° C. Aliquots (25 µL) were taken at various time intervals (1 h, 4 h, 24 h, 96 h, 7 days) and quenched with acetonitrile/0.1% TFA (1:1, 100 µL). The samples were centrifuged, and the supernatants were analyzed by radio-HPLC. No degradation products were observed over 1 week.

Determination of Partition Coefficient (log $D_{7.4}$)

The lipophilicity of $^{177}$Lu-14 (FAUC Lu469) was assessed by determination of the water-octanol partition coefficient. 1-Octanol (0.5 mL) was added to a solution of approximately 25 kBq of $^{177}$Lu-14 in PBS (0.5 mL, pH 7.4) and the layers were vigorously mixed for 3 min at room temperature. The tubes were centrifuged (14000 rpm, 1 min) and three samples of 100 µL of each layer were counted in a γ-counter (Wallac Wizard). The partition coefficient was determined by calculating the ratio cpm (octanol)/cpm (PBS) and expressed as log $D_{7.4}$) log(cpm$_{octanol}$/cpm$_{buffer}$). The experiments were performed in triplicates. The log $D_{7.4}$ value was determined to be −1.8±0.1 (mean value±standard deviation, n=6).

Animal Models

Athymic nude mice (nu/nu) were obtained from Harlan Winkelmann GmbH (Borchen, Germany) at 4 weeks of age and were kept under standard conditions (12 h light/dark) with food and water available ad libitum. AsPC-1, PC-3 or HT29 cells were harvested and suspended in sterile PBS at a concentration of 2×10$^7$ cells/ml. Viable cells (2×10$^6$) in PBS (100 µL) were injected subcutaneously in the back. Two weeks after inoculation (tumor weight: 400-800 mg), the mice (about 10-12 weeks old with about 40 g body weight) were used for biodistribution studies.

Biodistribution Studies

The xenografted mice were injected with $^{177}$Lu-14 (FAUC Lu469, 1 MBq/mouse) intravenously into the tail vein. The mice were sacrificed by cervical dislocation at 24 h and 48 h post-injection (p.i.). Tumors and other tissues (blood, lung, liver, kidneys, heart, brain, muscle and intestine) were removed and weighed. Radioactivity of the dissected tissues was determined using a γ-counter. Results were expressed as percentage of injected dose per gram of tissue (% ID/g), and tumor-to-organ ratios were calculated. Results are reported as percent injected dose per gram (% ID/g) in Table 2 and FIG. 1.

TABLE 2

Uptake expressed as % ID/g of $^{177}$Lu-14 (FAUC Lu469) in different tumors and normal tissue at 24 h and 48 h p.i.

| | Biodistribution 24 h p.i. | | | Biodistribution 48 h p.i. | | |
|---|---|---|---|---|---|---|
| organ | mean | SD | N | mean | SD | N |
| blood | 0.36 | 0.08 | 8 | 0.14 | 0.05 | 8 |
| lung | 4.15 | 4.80 | 8 | 1.23 | 0.42 | 8 |
| liver | 11.61 | 4.68 | 8 | 5.45 | 0.73 | 8 |
| kidney | 4.54 | 0.43 | 4 | 2.48 | 0.66 | 7 |
| heart | 1.05 | 0.58 | 8 | 0.56 | 0.17 | 8 |
| spleen | 2.40 | 1.00 | 8 | 1.60 | 0.27 | 8 |
| brain | 0.06 | 0.02 | 8 | 0.04 | 0.01 | 8 |
| muscle | 0.29 | 0.04 | 8 | 0.19 | 0.06 | 8 |
| femur | 0.89 | 0.21 | 8 | 0.75 | 0.19 | 8 |
| HT29 | 18.64 | na | 1 | 16.34 | 1.23 | 2 |
| PC3 | 15.57 | 2.42 | 2 | 10.85 | 0.98 | 2 |
| intestine | 1.40 | 0.18 | 8 | 0.77 | 0.17 | 8 |
| AsPC1 | 22.36 | 3.33 | 2 | 14.41 | 4.19 | 2 |

For comparison, biodistribution studies conducted with reference compound 2 showed a AsPC1-tumor uptake of 34.2±2.5% ID/g (2) at 24 h p.i., together with low kidney (0.9±0.5% ID/g) and liver (1.5±0.5% ID/g) uptake. However, the retention of reference compound 2 in the AsPC1 tumor (4.6±2.2% ID/g at day 7 p.i., n=2) was significantly lower than the AsPC1-tumor retention of FAUC Lu469

(13.2±2.1% ID/g at day 7 p.i., n=2), indicating the favourable radiation dosimetry of FAUC Lu469 for radiotherapy.

Therapy Study Concerning $PC_{1-3}$ Tumors Using Single-Dose Administration

Nude mice bearing $PC_{1-3}$ tumors at the back were used for the therapy study. One week after inoculation of the $PC_{1-3}$ cells, $^{177}$Lu-14 (FAUC Lu469) was injected in four mice at a dose of 30±9 MBq/animal. Eight additional animals were injected with saline as control animals. The body weight and the tumor diameter was measured every three days. The result of the tumor growth over time after starting the treatment is shown in FIG. 2. Animals injected with $^{177}$Lu-14 (FAUC Lu469) showed a significantly inhibited tumor growth and a reduction in tumor size in comparison with untreated control animals. The tumor inhibition growth factor was 64% after 49 days. Consequently, the treated animals showed significantly longer survival than the untreated control animals (FIG. 2).

Figure 3:
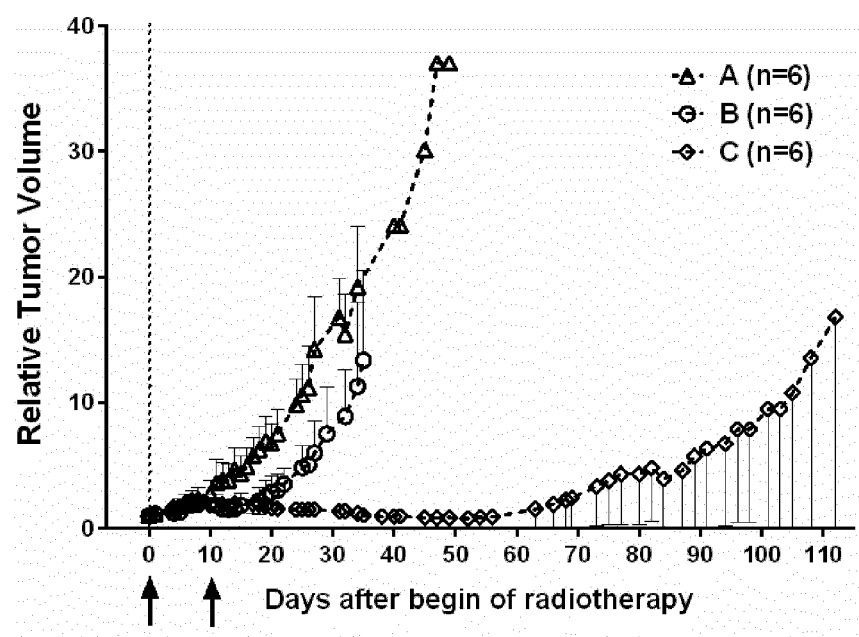
FIG. 3 shows experimental data on endoradiotherapy with FAUC Lu469 in AsPC-1 pancreas tumor-bearing nude mice. Single-dose administration (group B, 1×28 MBq/animal) in comparison with double-dose administration (group C, 2×29 MBq/animal) and untreated control animals (group A).

Therapy Study Concerning AsPC-1 Tumors Using Single-Dose Administration and Double-Dose Administration Nude mice bearing AsPC-1 tumors (human pancreas adenocarcinoma) at the back were used for the therapy study. One week after inoculation of the AsPC-1 cells, six mice were injected with a single dose of $^{177}$Lu-14 (FAUC Lu469) (28±6 MBq/animal, group B, single-dose administration) at day 0 and another six animals were injected with a double-dose of $^{177}$Lu-14 (FAUC Lu469) (2×29±4 MBq/animal, group C, double-dose administration), consisting of the first dose (29 MBq/animal) at the starting day of radiotherapy (day 0) and the second dose (29 MBq/animal) at day 10 after begin of treatment. Six additional animals were injected with saline as untreated control animals (group A). The body weight and the tumor diameter were measured five times a week. The results of the tumor growth over time after starting the treatment are shown in FIG. 3. Animals injected with a single dose of $^{177}$Lu-14 (FAUC Lu469) showed significant tumor growth inhibition and a reduction in tumor size between day 11 and 21 after begin of therapy in comparison with untreated control animals (adjusted p=0.049, n=6). The animals which received $^{177}$Lu-14 (FAUC Lu469) by double-dose administration (group C) demonstrated significantly longer survival (+209%) than the untreated control animals (FIG. 3).

As has been shown by the above examples, the present invention provides radiopharmaceuticals that show low binding to dopamine receptors and improved selectivity for NTS1. This increased selectivity improves the achievable data quality in diagnosis and imaging of NTS1-positive tumors and thus opens new opportunities for early detection of NTS1-positive tumors. Furthermore, the increased selectivity along with the excellent activity of the compounds of the present invention is expected to provide new therapeutic opportunities, in particular in the treatment of cancer.

The invention claimed is:

1. A compound of formula (I), optionally in the form of a pharmaceutically acceptable salt, solvate, ester, polymorph, tautomer, racemate, enantiomer, diastereomer or mixture thereof

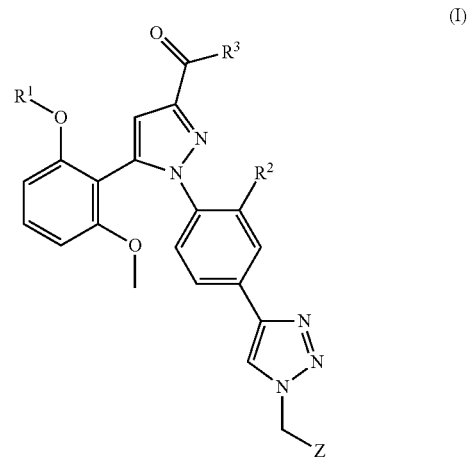

wherein:
$R^1$ is selected from the group consisting of -hydrogen, -($C_{1-6}$ alkyl), —($C_{3-6}$ cycloalkyl) and -($C_{1-3}$ alkylene-$C_{3-6}$ cycloalkyl), wherein $C_{1-6}$ alkyl, $C_{3-6}$ cycloalkyl and the $C_{1-3}$ alkylene and $C_{3-6}$ cycloalkyl in ($C_{1-3}$ alkylene-$C_{3-6}$ cycloalkyl) may be substituted with one or more halogen atoms, $R^2$ is selected from -hydrogen, -halogen, nitro, —($C_{1-6}$ alkyl), —($C_{3-6}$ cycloalkyl) and -($C_{1-3}$ alkylene-$C_{3-6}$ cycloalkyl), wherein $C_{1-6}$ alkyl, $C_{3-6}$ cycloalkyl and the $C_{1-3}$ alkylene and $C_{3-6}$ cycloalkyl in ($C_{1-3}$ alkylene-$C_{3-6}$ cycloalkyl) may be substituted with one or more halogen atoms, $R^3$ is selected from 2-amino-2-adamantane carboxylic acid, cyclohexylglycine and 9-amino-bicyclo[3.3.1]nonane-9-carboxylic acid, and Z comprises a chelator group.

2. The compound of formula (I) according to claim 1, wherein $R^3$ is

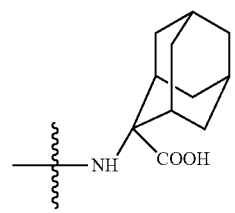

3. The compound of formula (I) according to claim 1, wherein the chelator group is -(hydrocarbon group which contains from 8 to 40 carbon atoms and 2 to 12 nitrogen atoms, and optionally contains 1 to 10 oxygen atoms, 1 to 5 sulfur atoms, 1 to 5 phosphor atoms, or a combination thereof).

4. The compound of formula (I) according to claim 1, wherein the chelator group is selected from 1,4,7,10-tetraazacyclododecane-1,4,7,10-tetraacetic acid (DOTA), 2,2',2''-(1,4,7-triazonane-1,4,7-triyl)triacetic acid (NOTA), 1,4,7-triazacyclononane-1,4-diiacetic acid (NODA), N,N'-bis-[2-hydroxy-5-(carboxyethyl)benzyl]ethylenediamine-N,N'-diacetic acid (HBED-CC), 3,6,9,15-tetraazabicyclo[9.3.1]pentadeca-1(15),11,13-triene-3,6,9,-triacetic acid (PCTA), diethylenetriaminepentaacetic acid (DTPA), N'-{5-[acetyl(hydroxy)amino]pentyl —N45-({4-[(5-aminopentyl)(hydroxy)amino]-4-oxobutanoyl}amino)pentyl]-N-hydroxysuccinamide (DFO), 1,4,8,11-tetraazacyclododecane-1,4,8,11-tetraacetic acid (TETA), ethylenediamine-N,N'-tetraacetic acid (EDTA), 1,4,7-triazacyclononane-N-glutaric acid-N',N''-diacetic acid (NODAGA), 1,4,7- triazacyclononane-1-succinic acid-4,7-diacetic acid (NODASA), 1,4,7,10 tetraazacyclotridecane-1,4,7,10-tetraacetic acid (TRITA), trans-1,2-diaminocyclohexane-N,N,N',N'-tetraacetic acid (CDTA), 1-[2-(2-mercapto-2-methyl-propylamino)-ethylamino]-2-methyl-propane-2-thiol (BAT), 6-hydrazino-nicotinic acid (HYNIC), 1,4,7-triazacyclononane-1,4-bis[methylene(hydroxymethyl)phosphinic acid]-7-[methylene(2-carboxyethyl)phosphinic acid] and 1,4,7-triazacyclononane phosphinic acid.

5. The compound of formula (I) according to claim 1, wherein the chelator group is

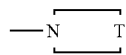

wherein T is $-[(CR^5_2)m(NR^6)]_q(CR^5_2)_m-$, wherein:
each $R^5$ is independently selected from -hydrogen, -halogen, —OH, -$C_{1-6}$ alkyl and -O-$C_{1-6}$ alkyl,
each $R^6$ is independently selected from -hydrogen, -$C_{1-6}$ alkyl, —($C_{1-6}$ alkylene)-COOH, —($C_{1-3}$ alkylene)-P(O)(OH)-($C_{1-3}$ alkylene)-COOH, and -($C_{1-3}$ alkylene)-P(O)(OH)-($C_{1-3}$ alkylene)-OH,
each m is independently an integer from 1 to 4, and
q is an integer from 3 to 5.

6. The compound of formula (I) according to claim 1, wherein Z is -(linker group)-(chelator group) and the linker group is $-(X)_p-$, wherein:
p is an integer from 1 to 10, and
each X is independently selected from:
(a) —N($R^4$)-$C_{1-10}$ alkylene)-,
(b) —N($R^4$)-heteroarylene)-,
(c) —N($R^4$)-C(O))-,
(d) —(O-$C_{1-10}$ alkylene)-,
(e) —(O-heteroarylene)-,
(f) —(O-C(O))-,
(g) —($C_{1-10}$ alkylene-heteroarylene)-,
(h) —($C_{1-10}$ alkylene-C(O))-,
(i) —(C(O)-$C_{1-10}$ alkylene)-,
(j) —(C(O)-heteroarylene)-,
(k) —(heteroarylene-$C_{1-10}$ alkylene)-,
(l) —(heteroarylene-C(O))-, and
(m) —($C_{1-10}$ alkylene)-,
wherein each $C_{1-10}$ alkylene is independently optionally substituted with one or more selected from halogen, C(O)OH, and OH,
wherein heteroarylene is 4 to 6-membered heteroarylene comprising 1 to 3 heteroatoms selected from N, O, and S, and wherein the heteroarylene is optionally substituted with one or more selected from halogen and $C_{1-6}$ alkyl; and
wherein each $R^4$ is independently selected from hydrogen and $C_{1-6}$ alkyl.

7. The compound of formula (I) according to claim 6, wherein the linker group is selected from:
(i) —$C_{1-10}$ alkylene-N($R^4$)-$C_{1-10}$ alkylene-N($R^4$)-C(O)-$C_{1-10}$ alkylene- N($R^4$)-,
(ii) —$C_{1-10}$ alkylene-N($R^4$)-$C_{1-10}$ alkylene-heteroarylene-$C_{1-10}$ alkylene-C(O)-$C_{1-10}$ alkylene- N($R^4$)-, and
(iii) —$C_{1-10}$ alkylene-N($R^4$)-$C_{1-10}$ alkylene-N($R^4$)-, wherein each $C_{1-10}$ alkylene is independently optionally substituted with one or more selected from halogen, C(O)OH, and OH,
wherein heteroarylene is 4 to 6-membered heteroarylene comprising 1 to 3 heteroatoms selected from N, O, and S, and wherein the heteroarylene is optionally substituted with one or more selected from halogen and $C_{1-6}$ alkyl, and
wherein each $R^4$ is independently selected from hydrogen and $C_{1-6}$ alkyl.

8. A composition or complex, optionally in the form of a pharmaceutically acceptable salt, solvate, ester, polymorph, tautomer, racemate, enantiomer, or diastereomer or mixture thereof, the composition or complex comprising:
the compound of formula (I) according to claim 1; and
one or more diagnostically or therapeutically effective radionuclides.

9. A process comprising reacting the compound of formula (I) according to claim 1 with one or more diagnostically or therapeutically effective radionuclides to provide a complex of the compound of formula (I) with the one or more diagnostically or therapeutically effective radionuclides.

10. The process according to claim 9, wherein the reaction is carried out in a solvent comprising water, and wherein the reaction is carried out at a temperature in the range from 20° C. to 100° C.

11. The process according to claim 9, wherein the complex is formed into a pharmaceutically acceptable salt, solvate, ester, polymorph, tautomer, racemate, enantiomer, or diastereomer or mixture thereof.

12. The composition or complex according to claim 8, wherein the composition or complex is configured for use in the diagnosis or treatment of a disorder comprising a tumor or hematological malignancy.

13. The composition or complex according to claim 12, wherein the disorder is a disorder involving a neurotensin receptor.

14. The composition or complex according to claim 8, further comprising a pharmaceutically acceptable excipient.

15. A kit comprising the compound of formula (I) according to claim 1 and one or more radionuclides.

16. The compound of formula (I) according to claim 1, further comprising one or more diagnostically or therapeutically effective radionuclides reacted with the chelator group.

17. The compound according to claim 6, wherein each $R^4$ is independently selected from hydrogen, methyl, ethyl, n-propyl, and iso-propyl.

18. The composition or complex according to claim 8, wherein the radionuclide is selected from F-18, P-32, P-33, Sc-44, Sc-47, Cr-51, Fe-52, Fe-59, Mn-51, Mn-52m, Co-55, Co-57, Co-58, Cu-62, Cu-64, Cu-67, Ga-67, Ga-68, As-72, Se-75, As-77, Br-76, Br-75, Br-77, Br-80m, Br-82, Rb-82m, Sr-83, Sr-89, Y-86, Y-90, Zr-89, Mo-99, Tc-94m, Tc-99m, Ru-97, Rh-103m, Rh-105, Pd-109, Pt-109, Ag-111, In-110, In-111, In-113m, In-114m, Sb-119, Sn-121, Te-127, 1-120, 1-123, 1-124, 1-125, 1-129, 1-131, Pr-142, Pr-143, Pm-149, Pm-151, Sm-153, Dy-152, Dy-166, Gd-157, Gd-159, Ho-161, Tb-161, Ho-166, Er-169, Tm-172, Yb-169, Yb-175, Lu-177, Lu-177m, Re-186, Re-188, Re-189, Rd-188, Os-189m, Ir-192, Ir-194, Au-198, Au-199, Hg-197, Tl-201, Pb-203, Pb-211, Pb-212, Bi-211, Bi-212, Bi-213, At-211, At-217, Po-215, Ra-223, Rn-219, Fr-221, Ac-225, Th-227, and Fm-255.

19. The process according to claim 10, wherein the solvent further comprises a buffer.

* * * * *